US011999966B2

(12) United States Patent
Hjort et al.

(10) Patent No.: US 11,999,966 B2
(45) Date of Patent: Jun. 4, 2024

(54) APPARATUSES AND METHODS USING NANOSTRAWS TO DELIVER BIOLOGICALLY RELEVANT CARGO INTO NON-ADHERENT CELLS

(71) Applicant: The Board of Trustees of the Leland Stanford Junior University, Stanford, CA (US)

(72) Inventors: Karl Martin Hjort, Lund (SE); Sergio Leal-Ortiz, Hayward, CA (US); Yuhong Cao, Palo Alto, CA (US); Chris Rehse, Palo Alto, CA (US); Andy Kah Ping Tay, Stanford, CA (US); Nicholas A. Melosh, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 479 days.

(21) Appl. No.: 17/081,983

(22) Filed: Oct. 27, 2020

(65) Prior Publication Data
US 2021/0062222 A1    Mar. 4, 2021

Related U.S. Application Data

(63) Continuation of application No. 16/038,062, filed on Jul. 17, 2018, now Pat. No. 10,815,499.
(Continued)

(51) Int. Cl.
*C12N 15/87*    (2006.01)
*B82Y 5/00*    (2011.01)
(Continued)

(52) U.S. Cl.
CPC .............. *C12N 15/87* (2013.01); *C12M 23/02* (2013.01); *C12M 23/42* (2013.01); *C12M 35/00* (2013.01);
(Continued)

(58) Field of Classification Search
CPC .... C12N 15/87; C12N 5/0075; C12N 5/0068; C12N 2521/00; C12N 2535/00;
(Continued)

(56) References Cited

U.S. PATENT DOCUMENTS 6,368,851 B1    4/2002    Baumann et al.
7,152,616 B2    12/2006    Zucchelli et al.
(Continued)

FOREIGN PATENT DOCUMENTS

CN    1286716 C    11/2006
CN    102656260 A    9/2012
(Continued)

OTHER PUBLICATIONS

Chang et al.; Dielectrophoresis-assisted 3D nanoelectroporation for non-viral cell transfection in adoptive immunotherapy. Lab on a Chip. 15(15); pp. 3147-3153; Jun. 2015.
(Continued)

*Primary Examiner* — Sean C. Barron
(74) *Attorney, Agent, or Firm* — Rimon PC

(57) ABSTRACT

Nanostraws and to methods of utilizing them in order to deliver biologically relevant molecules such as DNA, RNA, proteins etc., into non-adherent cells such as immune cells, embryos, plant cells, bacteria, yeast etc. The methods described herein are repeatedly capable of delivering biologically relevant cargo into non-adherent cells, with high cell viability, dosage control, unaffected proliferation or cellular development, and with high efficiency. Among other uses, these new delivery methods will allow to scale pre-
(Continued)

clinical cell reprogramming techniques to clinical applications.

10 Claims, 13 Drawing Sheets

Related U.S. Application Data

(60) Provisional application No. 62/534,511, filed on Jul. 19, 2017.

(51) Int. Cl.
| | | |
|---|---|---|
| B82Y 40/00 | (2011.01) | |
| C12M 1/00 | (2006.01) | |
| C12M 1/42 | (2006.01) | |
| C12M 3/00 | (2006.01) | |
| C12M 3/06 | (2006.01) | |
| C12N 5/00 | (2006.01) | |

(52) U.S. Cl.
CPC ............ *C12M 35/02* (2013.01); *C12M 35/04* (2013.01); *B82Y 5/00* (2013.01); *B82Y 40/00* (2013.01); *C12M 23/16* (2013.01); *C12N 5/0068* (2013.01); *C12N 5/0075* (2013.01); *C12N 2521/00* (2013.01); *C12N 2535/00* (2013.01)

(58) Field of Classification Search
CPC ...... C12M 23/42; C12M 35/02; C12M 35/04; C12M 23/02; C12M 35/00; C12M 23/16; B82Y 40/00; B82Y 5/00
See application file for complete search history.

(56) References Cited

U.S. PATENT DOCUMENTS

| | | |
|---|---|---|
| 7,160,532 B2 | 1/2007 | Liu et al. |
| 8,808,516 B2 | 8/2014 | Melosh et al. |
| 9,266,725 B2 | 2/2016 | Vandersarl et al. |
| 9,304,132 B2 | 4/2016 | Park et al. |
| 9,856,448 B2 | 1/2018 | Melosh et al. |
| 10,150,947 B2 | 12/2018 | Vandersarl et al. |
| 10,815,499 B2 | 10/2020 | Hjort et al. |
| 2004/0182707 A1 | 9/2004 | Jardemark et al. |
| 2006/0213259 A1 | 9/2006 | Prinz et al. |
| 2007/0100086 A1 | 5/2007 | Hong et al. |
| 2008/0302960 A1 | 12/2008 | Meister et al. |
| 2009/0220561 A1 | 9/2009 | Jin et al. |
| 2010/0035322 A1 | 2/2010 | Raffa et al. |
| 2010/0140111 A1 | 6/2010 | Gimsa et al. |
| 2010/0215724 A1 | 8/2010 | Prakash et al. |
| 2011/0168968 A1 | 7/2011 | Yang et al. |
| 2011/0208031 A1 | 8/2011 | Wolfe et al. |
| 2012/0040370 A1 | 2/2012 | Orwar et al. |
| 2012/0225435 A1 | 9/2012 | Seger et al. |
| 2012/0264108 A1 | 10/2012 | Chen et al. |
| 2013/0118621 A1 | 5/2013 | Weber et al. |
| 2014/0342445 A1 | 11/2014 | Ingber et al. |
| 2015/0197807 A1 | 7/2015 | Park et al. |
| 2016/0032275 A1 | 2/2016 | Actis et al. |
| 2016/0201030 A1* | 7/2016 | Vandersarl ............... B82Y 5/00 435/367 |
| 2019/0119629 A1 | 4/2019 | Vandersarl et al. |
| 2019/0359974 A1 | 11/2019 | Melosh et al. |
| 2019/0365803 A1 | 12/2019 | Melosh et al. |
| 2019/0367861 A1 | 12/2019 | Swoboda et al. |

FOREIGN PATENT DOCUMENTS

| | | |
|---|---|---|
| JP | 11346764 A | 12/1999 |
| JP | 2003501639 A | 1/2003 |
| JP | 2003505073 A | 2/2003 |
| JP | 2009541198 A | 11/2009 |
| WO | WO2002/058847 A2 | 8/2002 |
| WO | WO2009/063776 A1 | 3/2011 |
| WO | WO2017/027549 A1 | 2/2017 |
| WO | WO2017/214541 A1 | 12/2017 |

OTHER PUBLICATIONS

Chang et al.; Magnetic tweezers-based 3D microchannel electroporation for high-throughput gene transfection in living cells; Small; 11(15); pp. 1818-1828; 20 pages (Author Manuscript); Apr. 2015.

Wu et al.; Efficient expression of foreign genes in human CD34+ hematopoietic precursor cells using electroporation; Gene Therapy; 8(5);, pp. 384-390; Mar. 2001.

Baek et al.; Gene transfection for stem cell therapy; Current Stem Cell Reports; 2(1); pp. 52-61; Jan. 27, 2016.

Schmiderer et al.; Efficient and nontoxic biomolecule delivery to primary human hematopoietic stem cells using nanostraws; Proceedings of the National Academy of Sciences; 117(35); pp. 21267-21273; Sep. 2020.

Abhyankar et al.; Characterization of a membrane-based gradient generator for use in cell-signaling studies; Lab Chip; 6(3):389-393; Mar. 2006.

Actis et al.; Compartmental genomics in living cells revealed by single-cell nanobiopsy; ACS Nano; 8(1); pp. 546-553; Jan. 28, 2014.

Adler et al.; Emerging links between surface nanotechnology and endocytosis: impact on nonviral gene delivery; Nano Today; 5(6):553-569; Dec. 2010 (author manuscript, 15 pgs.).

Ainslie et al.; Microfabricated devices for enhanced bioadhesive drug delivery: attachment to and small-molecule release through a cell monolayer under flow; Small; 5(24):2857-2863; Dec. 2009.

Almquist et al.; Fusion of biomimetic stealth probes into lipid bilayer cores; Proc Natl Acad Sci U S A.; 107(13):5815-5820; Mar. 2010.

Almquist et al.; Nanoscale patterning controls inorganic-membrane interface structure; Nanoscale; 3(2):391-400; Feb. 2011.

Bancroft et al.; Fluid flow increases mineralized matrix deposition in 3D perfusion culture of marrow stromal osteoblasts in a dose-dependent manner; PNAS; 99(20):12600-12605; Oct. 1, 2002.

Bernards et al.; Nanoscale porosity in polymer films: fabrication and therapeutic applications; Soft Matter; 6(8):1621-1631; Jan. 2010 (author manuscript, 13 pgs.).

Black et al.; Upregulation of a silent sodium channel after peripheral, not not central, nerve injury in DRG neurons; J Neurophysiol; 82(5); pp. 2776-2785; Nov. 1999.

Boyden; The chemotactic effect of mixtures of antibody and antigen on polymorphonuclear leucocytes; J Exp Med; 115:453-466; Mar. 1, 1962.

Cao et al.; Template-based synthesis of nanorods, nanowire and nanotube array; Adv Colloid Interface Sci; 136(1-2):45-64; Jan. 15, 2008.

Cao et al.; Non destructive nanostraw intracellular sampling for longitudinal cell monitoring; Proceedings of the National Academy of Sciences; 114(10); pp. E1866-E1874; XP002797487; Mar. 1, 2017.

Carter; Potent antibody therapeutics by design; Nat Rev Immunol; 6(5):343-57; May 2006.

Chen et al.; A cell nanoinjector based on carbon nanotubes; Proc Natl Acad Sci U S A.; 104(20):8218-8222; May 15, 2007.

Choi; A Cellular Trojan Horse for Delivery of Therapeutic Nanoparticles into Tumors. Nano Letters; 7(12), pp. 3759-3765; Dec. 2007.

Chu et al.; Electroporation for the efficient transfection of mammalian cells with DNA; Nucleic Acids Res.; 15(3):1311-1326; Feb. 11, 1987.

Das et al.; TiO2 nanotubes on Ti: influence of nanoscale morphology on bone cell-materials interaction; Journal of Biomedical Materials Research Part A; 90(1); pp. 225-237; Jun. 1, 1990.

Daub et al.; Ferromagnetic nanotubes by atomic layer deposition in anodic alumina membranes; J. Appl. Phys.: 101; 09J111 (4 pgs.); May 2007.

(56) References Cited

OTHER PUBLICATIONS

Dertinger et al.; Generation of Gradients Having Complex Shapes Using Microfluidic Networks; Anal Chem; 73:1240-1246; Feb. 16, 2001.
Diao et al.; A three-channel microfluidic device for generating static linear gradients and its application to the quantitative analysis of bacterial chemotaxis; Lab Chip; 6(3):381-388; Mar. 2006.
Dubey et al.; Intercellular nanotubes mediate bacterial communication; Cell; 144(4):590-600; Feb. 2011.
El-Ali et al.; Cells on Chips; Nature; 442(7101):403-411; Jul. 27, 2006.
Engler et al.; Matrix Elasticity Directs Stem Cell Lineage Specification; Cell; 126(4):677-689; Aug. 25, 2006.
Ertan et al.; Electrodeposition of nickel nanowires and nanotubes using various templates; Journal of Experimental Nanoscience; 3 (4); pp. 287-295; Dec. 2008.
Gasiorowski et al.; Alterations in gene expression of human vascular endothelial cells associated with nanotopographic cues; Biomaterials; 31(34):8882-8; Dec. 2010 (author manuscript, 15 pgs.).
Geldof; Nerve-growth-factor-dependent neurite outgrowth assay; a research model for chemotherapy-induced neuropathy; J Cancer Res Clin Oncol; 121(11):657-660; Feb. 1995.
Gheith et al.; Stimulation of Neural Cells by Lateral Currents in Conductive Layer-by-Layer Films of Single-Walled Carbon Nanotubes; Adv Mater; 18(22):2975-2979; Nov. 2006.
Giancotti et al.; Integrin signaling; Science; 285(5430):1028-1032; Aug. 13, 1999.
Goetz et al; Computer simulations of bilayer membranes: Self-assembly and interfacial tension; J Chem Phys; 108(7):7397-7409; May 1, 1998.
Griffith et al.; Polymeric biomaterials; Acta Mater; 48(1):263-277; Jan. 1, 2000.
Hanna et al.; Direct cell reprogramming is a stochastic process amenable to acceleration; Nature;462(7273):595-601; Dec. 2009 (auhor manuscript, 17 pgs.).
Haydon et al.; Anaesthesia by the n-alkanes. A comparative study of nerve impulse blockage and the properties of black lipid bilayer membranes; BBA—Biomembranes; 470(1):17-34; Oct. 3, 1977.
Haydon et al.; The molecular mechanisms of anaesthesia; Nature; 268:356-358; Jul. 28, 1977.
Heath et al.; Nanotechnology and cancer; Annu Rev Med; 59:251-65; Feb. 2008 (author manuscript, 16 pgs.).
James et al.; Patterned protein layers on solid substrates by thin stamp microcontact printing; Langmuir; 14(4); pp. 741-744; Jan. 1998.
Jeon et al.; Generation of Solution and Surface Gradients Using Microfluidic Systems; Langmuir; 16(22):8311-8316; Oct. 31, 2000.
Keenan et al.; Microfluidic jets for generating steady-state gradients of soluble molecules on open surfaces; Appl. Phys. Lett.; 89(11);114103-114103-3; Sep. 11, 2006.
Keenan et al.; Biomolecular gradients in cell culture systems; Lab Chip; 8(1):34-57; Jan. 2008.
Kim et al.; Interfacing Silicon Nanowires with Mammalian Cells; J Am Chem Soc; 129(23):7228-7229; Jun. 13, 2007.
Kinoshita; Electrochemical Uses of Carbon; Electrochem Encycl; pp. 11; Jan. 2001.
Knez et al.; Synthesis and Surface Engineering of Complex Nanostructures by Atomic Layer Deposition; Adv Mater; 19(21):3425-3437; Nov. 2007.
Kubota et al.; Role of laminin and basement membrane in the morphological differentiation of human endothelial cells into capillary-like structures; Journal of Cell Biology; 107; pp. 1589-1598; Oct. 1988.
Kumar et al.; The gap junction communication channel; Cell; 84(3):381-8; Feb. 1996.
Kwak et al.; Interfacing inorganic nanowire arrays and living cells for cellular function analysis; Small; 11(42); pp. 5600-5610; Nov. 11, 2015.
Langer; Drug delivery and targeting; Nature; 392(6679 Suppl):5-10.; Apr. 1998.

Langille et al.; Relationship between blood flow direction and endothelial cell orientation at arterial branch sites in rabbits and mice; Circ Res; 48(4):481-488; Apr. 1981.
Lee et al.; Hydrogels for tissue engineering; Chem Rev; 101(7):1869-1879; Jul. 2001.
Li et al.; Nanotube arrays in porous anodic alumina membranes; J. Mater. Sci. Tech.; 24(4); pp. 550-562; Jul. 2008.
Liu et al.; Voyage inside the cell: Microsystems and nanoengineering for intracellular measurement and manipulation, Microsystems & Nanoengineering; 1(1); XP055666437; DOI: 10.1038/micronano.2015.20; Sep. 14, 2015.
Loh et al.; Nanofountain-probe-based high-resolution patterning and single-cell injection of functionalized nanodiamonds; Small; 5(14):1667-1674; Jul. 2009.
Luo et al.; Synthetic DNA delivery systems; Nat Biotechnol; 18(1):33-7; Jan. 2000.
Lutolf et al.; Synthetic biomaterials as instructive extracellular microenvironments for morphogenesis in tissue engineering; Nat Biotecnol; 23(1):47-55; Jan. 2005.
Malboubi et al.; Effects of the Surface Morphology of Pipette Tip on Giga-seal Formation. Engineering Letters; 17(4), p. 281; Nov. 2009.
Martin; Nanomaterials: a membrane-based synthetic approach; Science; 266(5193): 1961-6.; Dec. 1994.
McKnight et al.; Tracking gene expression after DNA delivery using spatially indexed nanofiber arrays; Nano Letters; 4(7); pp. 1213-1219; May 2004.
Michalet et al.; Quantum dots for live cells, in vivo imaging, and diagnostics; Science; 307(5709):538-44; Jan. 28, 2005 (author manuscript; 16 pgs.).
Oates et al.; Role of titanium surface topography and surface wettability on focal adhesion kinase mediated signaling in fibroblasts; Materials; 4(5); pp. 893-907; May 9, 2011.
Patel, et al.; Spatially controlled cell engineering on biodegradable polymer surfaces; FASEB J; 12(14):1447-1454; Nov. 1998.
Peng et al.; Whole genome expression analysis reveals differential effects of TiO2 nanotubes on vascular cells; Nano Letters; 10(1); pp. 143-148; Jan. 2010.
Persson et al.; Vertical Nanotubes Connected by a Subsurface Nanochannel; 14th Int'l Conference on Miniturized Systems fror Chemistry and Life Sciences; 1862-1864; Oct. 3-7, 2010.
Petronilli et al.; Transient and long-lasting openings of the mitochondrial permeability transition pore can be monitored directly in intact cells by changes in mitochondrial calcein fluorescence; Biophys J.; 76(2):725-34.; Feb. 1999.
Plath et al.; Progress in understanding reprogramming to the induced pluripotent state; Nat Rev Genet.; 12(4):253-265; Apr. 2011 (author manuscript, 26 pgs.).
Qi; Cell adhesion and spreading behavior on vertically aligned silicon nanowire arrays; ACS Appl Mater Interfaces; 1(1):30-4; Jan. 2009.
Ruoslahti; New perspectives in cell adhesion: RGD and integrins; Science; 238(4826):491-7; Oct. 1987.
Safran et al.; Database update: GeneCards version 3: the human gene integrator; Database (Oxford); vol. 2010 (baq020); 16 pgs.; Aug. 2010.
Saito; A Theoretical Study on the Diffusion Current at the Stationary Electrodes of Circular and Narrow Band Types; Rev Polarography; 15(6):177-187; Dec. 1968.
Sakiyama-Elbert et al.; Controlled release of nerve growth factor from a heparin-containing fibrin-based cell ingrowth matrix; J Control Release; 69(1):149-158; Oct. 3, 2000.
Scadden; The stem-cell niche as an entity of action; Nature; 441(7097):1075-1079; Jun. 29, 2006.
Shalek et al.; Vertical silicon nanowires as a universal platform for delivering biomolecules into living cells; Proc Natl Acad Sci U S A.; 107(5):1870-1875; Feb. 2, 2010.
Sharei et al.; Ex Vivo Cytosolic Delivery of Functional Macromolecules to Immune Cells; PloS One; 10(4); e0118803, 12 pages; Jan. 7, 2015.
Shamloo et al.; Endothelial cell polarization and chemotaxis in a microfluidic device; Lab Chip; 8(8):1292-1299; Aug. 2008.

(56) References Cited

OTHER PUBLICATIONS

Sip et al.; Microfluidic transwell inserts for generation of tissue culture-friendly gradients in well plates; Lab on a Chip, 14(2); pp. 302-314; (year of pub. sufficiently earlier than effective US filing date and any foreign priority date); 2014.
Susin et al.; Molecular characterization of mitochondrial apoptosis-inducing factor; Nature; 397; pp. 441-446; Feb. 1999.
Tian et al.; Fabrication of high density metallic nanowires and nanotubes for cell culture studies; Microelectronic Eng; 88(8):1702-1706; Aug. 2011.
Tian et al.; Three-dimensional, flexible nanoscale field-effect transistors as localized bioprobes; Science;329(5993):830-4; Aug. 2010 (author manuscript, 11 pgs.).
Tiscornia et al.; A general method for gene knockdown in mice by using lentiviral vectors expressing small interfering RNA; Proc Natl Acad Sci U S.A.; 100(4):1844-1848; Feb. 18, 2003.
Uhrich et al.; Polymer systems for controlled drug release; Chem Rev; 99(11):3181-3198; Nov. 10, 1999.
Vandersarl et al.; Nanostraws for direct fluidic intracellular access; Nano Letters; 12(8); pp. 3881-3886; Dec. 20, 2011.
Verma et al.; Gigaohm resistance membrane seals with stealth probe electrodes; Appl Phys Lett; 97(3):1-3; Jul. 2010.
Verma et al.; Surface-structure-regulated cell-membrane penetration by monolayer-protected nanoparticles; Nat Mater; 7(7):588-595; Jul. 2008 (Author Manuscript; pp. 15).
Walker et al.; Effects of flow and diffusion on chemotaxis studies in a microfabricated gradient generator; Lab Chip; 5(6):611-618; Jun. 2005 (Author Manuscript; pp. 18).
Wang et al.; Neural stimulation with a carbon nanotube microelectrode array; Nano Lett; 6(9):2043-2048; Sep. 2006.
Wang et al.; Shear stress induces endothelial differentiation from a murine embryonic mesenchymal progenitor cell line; Arterioscler Thromb Vasc Biol; 25(9):1817-1823; Sep. 2005.
Whitesides; The origins and the future of microfluidics; Nature; 442(7101):368-373; Jul. 27, 2006.
Wolfe et al.; U.S. Appl. No. 61/306,778 entitled "Neutral Particle Nanopatterning for Nonplanar Multimodal Neural Probes," filed Feb. 22, 2010.
Wu et al.; Generation of complex, static solution gradients in microfluidic channels; J Am Chem Soc; 128(13):4194-4195; Apr. 5, 2006.
Xiao et al.; Fabrication of Alumina Nanotubes and Nanowires by Etching Porous Alumina Membranes; Nano Lett; 2(11):1293-1297; Oct. 26, 2002.
Xie et al.; Vertical nanopillars for highly localized fluorescence imaging; Proc Natl Acad Sci U S A.; 108(10):3894-9; Mar. 2011.
Xie et al.; Mechanical model of vertical nanowire cell penetration; Nano Letters; 13(12); pp. 6002-6008; Nov. 20, 2013.
Xie et al.; Nanostraw-Electroporation System for Highly Efficient Intracellular Delivery and Transfection; ACS Nano; 7(5); pp. 4351-4358; Apr. 18, 2013.
Yang et al.; Semiconductor nanowire: What's Next ?; Nano Letters; 10; pp. 1529-1536; May 2010.
Yu et al.; Diffusion dependent cell behavior in microenvironments; Lab Chip; 5(10):1089-1095; Oct. 2005.
Yu et al.; Nano Wheat Fields Prepared by Plasma-Etching Gold Nanowire-Containing Membranes; Nano Lett; 3(6);815-818; Mar. 20, 2003.
Zeck et al.; Noninvasive neuroelectronic interfacing with synaptically connected snail neurons immobilized on a semiconductor chip; Proc Natl Acad Sci U S A.; 98(18):10457-62; Aug. 2001.
Zicha et al.; A new direct-viewing chemotaxis chamber; J Cell Sci; 99(4);769-775; Aug. 1991.
Zigmond; Orientation chamber in chemotaxis; Methods Enzymol; 162:65-72; Oct. 12, 1988.

* cited by examiner

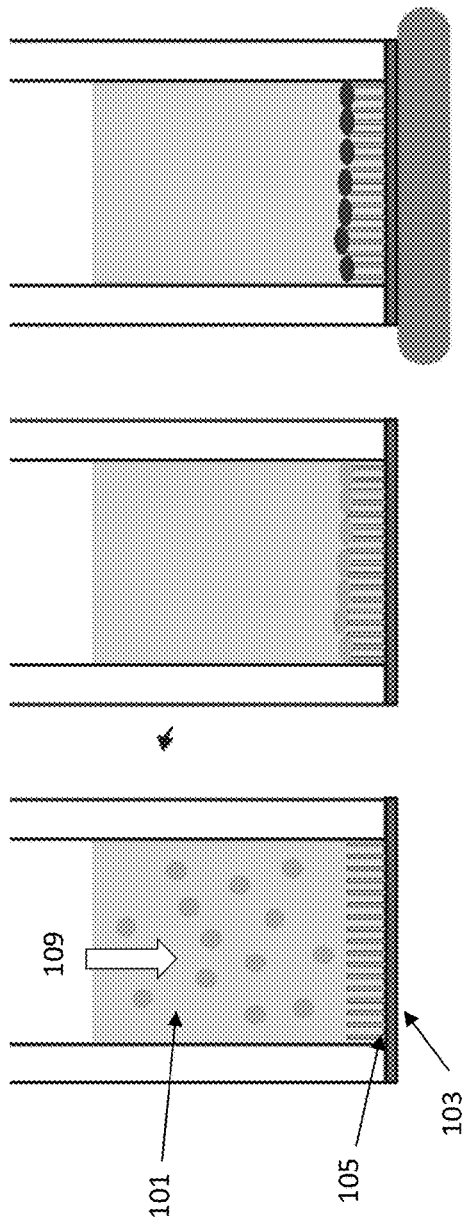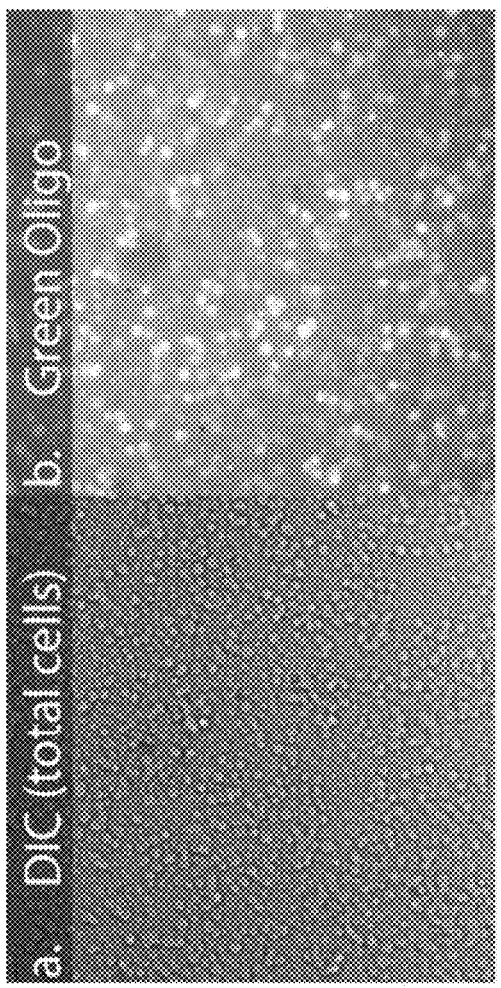

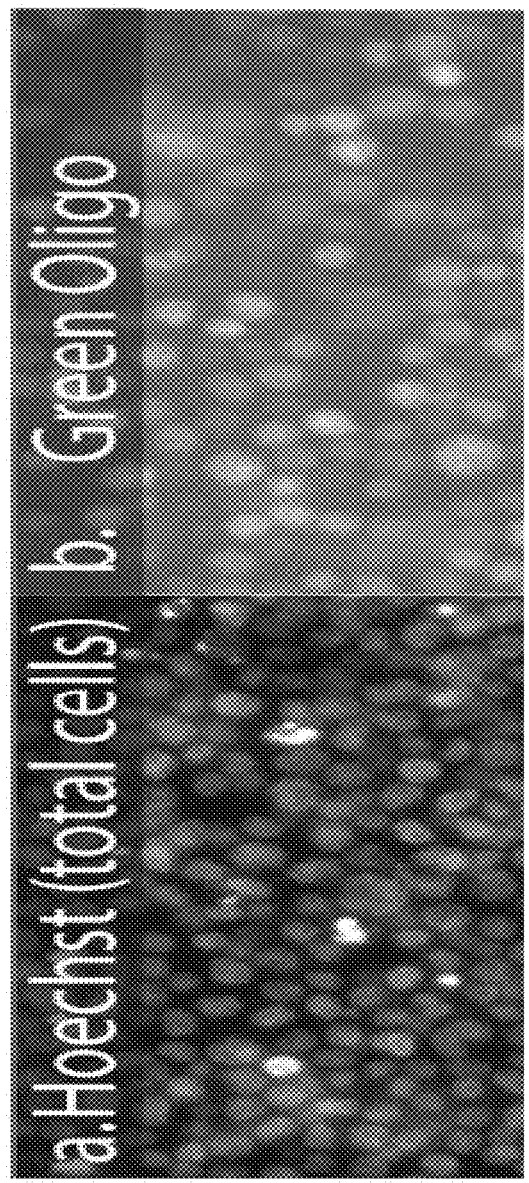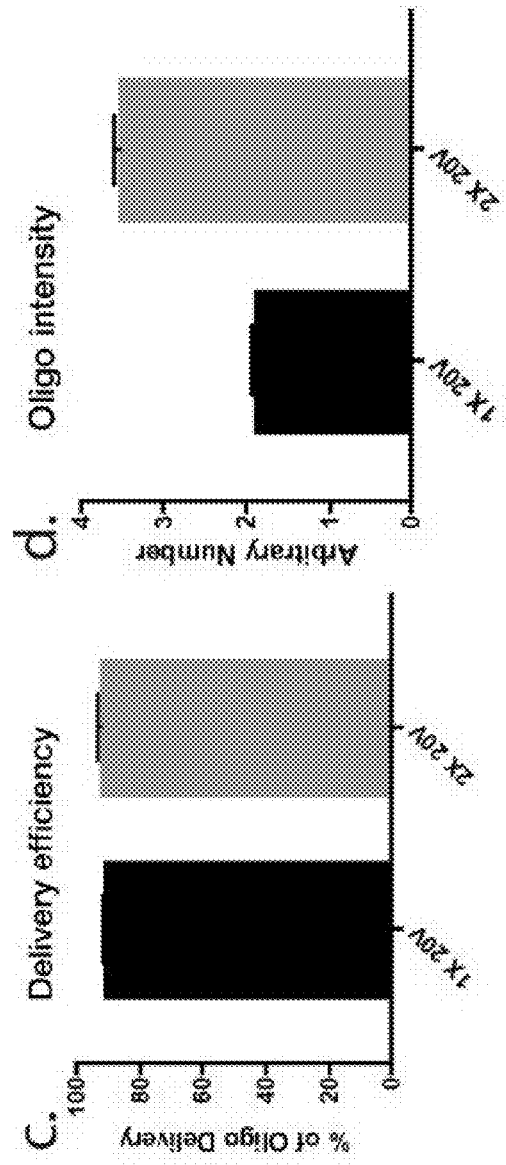
FIG. 3A  FIG. 3B  FIG. 3C  FIG. 3D

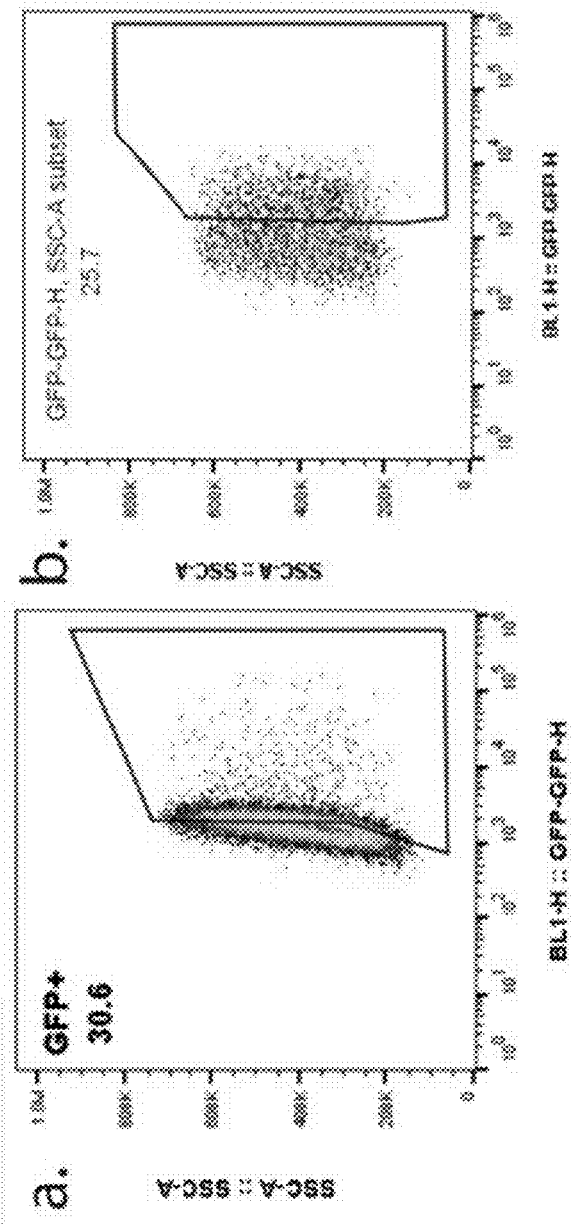
FIG. 4A
FIG. 4B
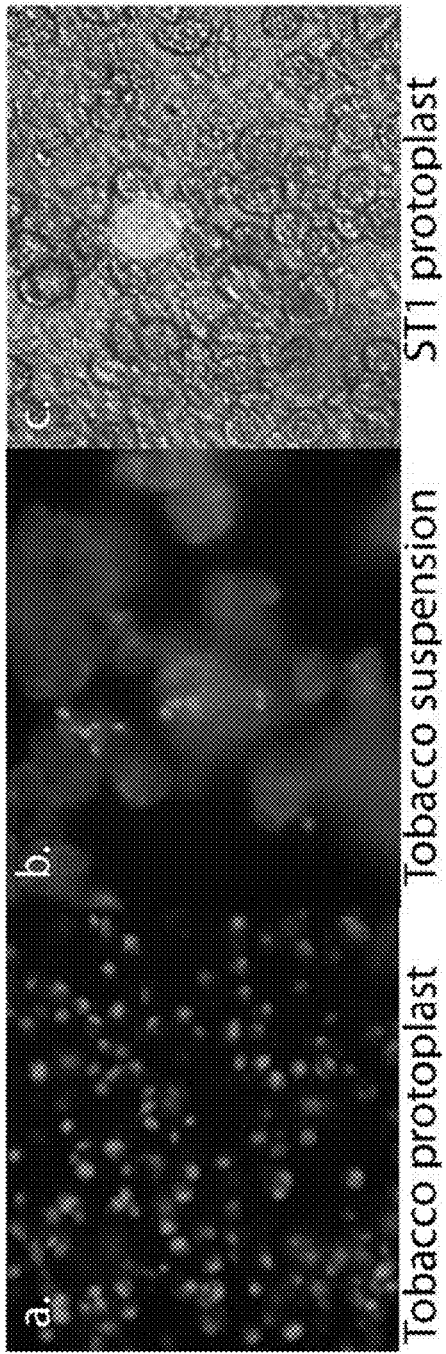
FIG. 5A  Tobacco protoplast
FIG. 5B  Tobacco suspension
FIG. 5C  ST1 protoplast

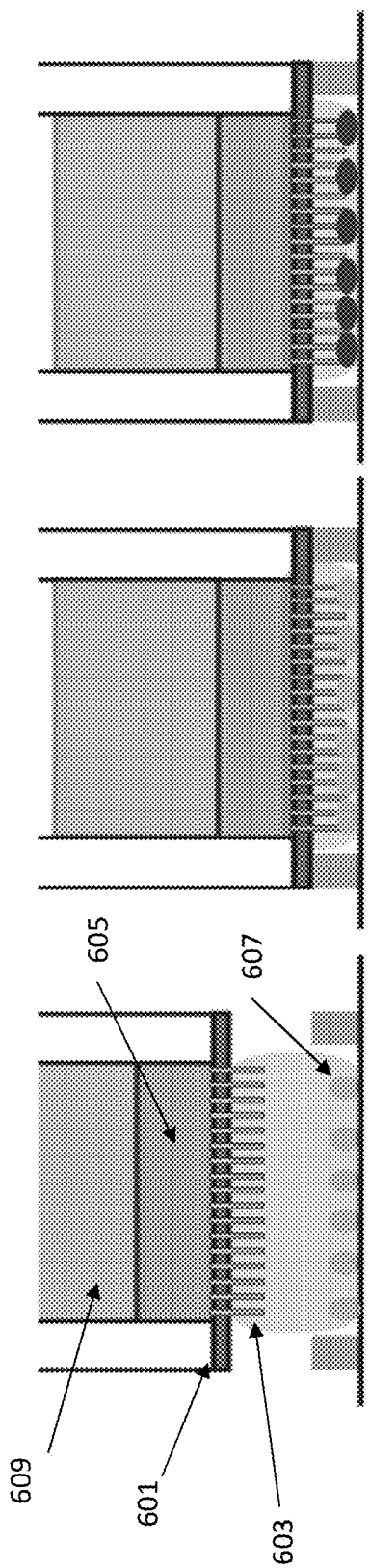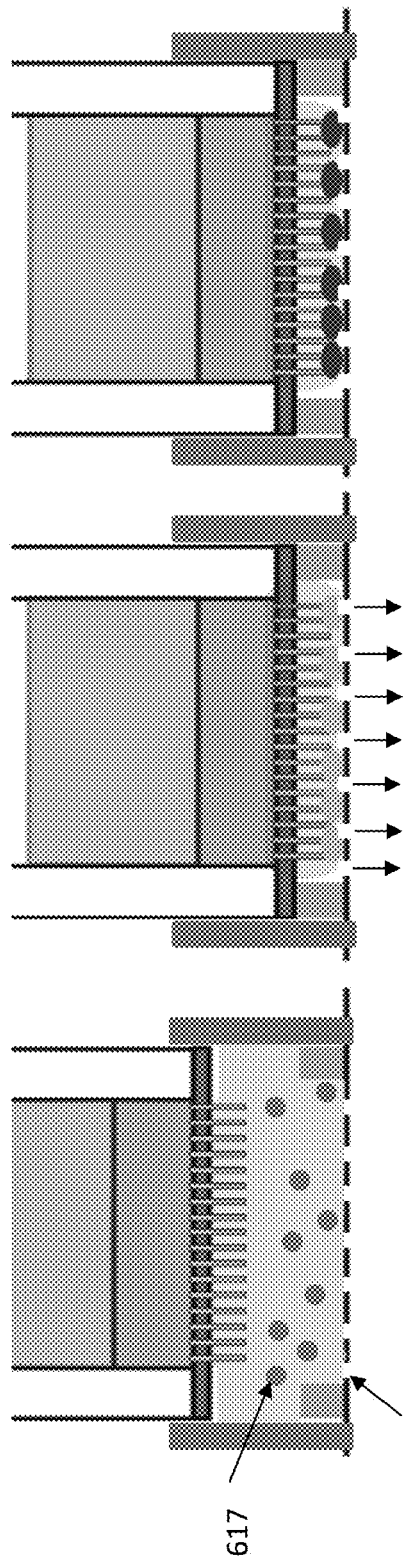

Dextran Blue

Calcein AM

PI Delivery
to Mouse Eggs

APPARATUSES AND METHODS USING NANOSTRAWS TO DELIVER BIOLOGICALLY RELEVANT CARGO INTO NON-ADHERENT CELLS

CROSS REFERENCE TO RELATED APPLICATIONS

This patent application is a continuation of U.S. patent application Ser. No. 16/038,062, filed Jul. 17, 2018, now U.S. Pat. No. 10,815,499 B2, which claims priority to U.S. Provisional Patent Application No. 62/534,511, filed Jul. 19, 2017, each of which is herein incorporated by reference in its entirety.

STATEMENT AS TO FEDERALLY SPONSORED RESEARCH

This work was made with Government support under contract 70NANB15H268 awarded by the National Institute of Standards & Technology and under contract 1549696 awarded by the National Science Foundation. The Government has certain rights in the invention.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Delivery of bio-molecules into cells is a crucial starting point for controlling cellular function, proliferation, differentiation, and apoptosis, among other things. Many bio-molecules will not spontaneously penetrate the cellular membrane, but rather need an external delivery method that will transport them into the intracellular space where they can perform certain tasks.

Non-adherent cells include, but is not limited to, blood cells, immune cells, adherent cells in the floatation stage, embryos, plant cells, fungi, yeast, and bacteria. Finding a general method to transport cargo through the cellular membrane for non-adherent cells is especially demanding since these cells come in a wide variety of sizes and with vastly different cell membrane properties.

Current methods to deliver into non-adherent cells have yielded low efficiencies, low cell viability, impacted cellular development or proliferation, been cargo specific, and/or was not suitable for sequential delivery. The lack of efficient delivery methods is currently a major hurdle that severely impacts research and commercial outcomes in fields spanning immunotherapy, gene therapy, agricultural development, transgenic animals, drug development, and much more.

Nanostraws have proven to be an efficient way to deliver biologically relevant cargo into cells. See, e.g., Vandersarl et al., Nano Letters. 12, 3881 (2012), and U.S. Pat. No. 9,266,725. U.S. Pat. No. 9,266,725 is hereby incorporated by reference in its entirety. Nanostraw usage have so far been limited to adherent cell types, thus limiting the use of nanostraws. It has been theorized that nanostraws can penetrate into non-adherent cells but that it is a highly unlikely event, in principle only applicable for nanostraw diameters much smaller than 50 nm, and longer than 5 μm. No studies have so far been presented that show nanostraw-mediated intracellular access for non-adherent cells. Such access would be of high scientific and commercial value as it would enable efficient and easy transformations of cells in industrially relevant topics such as immunotherapy, genetically modified organisms, and drug development.

SUMMARY OF THE DISCLOSURE

Described herein are nanostraws apparatuses and to methods of utilizing them in order to deliver biologically relevant molecules such as DNA, RNA (e.g., mRNA, microRNA, etc.), proteins etc., into non-adherent tissues, including both groups of cells and single cells, such as immune cells, embryos, plant cells, bacteria, yeast etc. Previous methods for delivering biologically relevant cargo into non-adherent cells yielded low efficiencies, and/or low cell viability, and/or impacted cell proliferation, and/or impacted cellular development, and/or was cargo specific, and/or was non-repeatable, and/or was without dosage control. By contrast, some of the methods described herein are repeatedly capable of delivering biologically relevant cargo into non-adherent cells, with high cell viability, dosage control, unaffected proliferation or cellular development, and with high efficiency. Among other uses, these new delivery methods will allow to scale pre-clinical cell reprogramming techniques to clinical applications.

Nanostraws are hollow metal-oxide nanotubes that extend from a surface. Nanostraws have been shown to be able to give direct access to the intracellular space of adherent cell types (cells that bind to a surface). The mechanism for gaining cellular access have been thought to be due to the cells gripping on to the surface and pulling themselves down onto the nanostraws by their own action, thereby stressing the cellular membrane just above the nanostraw tips. For that mechanism, it was hypothesized that only nanostraws of diameters smaller than about 50 nm and with very low areal density, would be able to give intracellular access for non-adherent cell types. Despite its industrial relevance, no data showing nanostraw-mediated intracellular access for non-adherent cells have been presented.

Herein described are apparatuses and methods that allow nanostraws (even of diameters larger than 50 nm) to gain intracellular access into non-adherent cells. The method is based on placing cells in a suspension in a container with nanostraws and coupling it with an external force that will enable the cells to interact with the nanostraws, thereby providing a close contact in between the cells and the nanostraws. This external force can be exerted through a number of mechanisms, including centrifugation, mechanical pressure (using magnetic beads, driving the nanostraws against the cell, etc.), electromagnetic force, etc. For example, min some variations, nanostraws may be mechanically pressed onto the cells. While in contact, biologically relevant cargo can be delivered into the cells through the nanostraws, which may be delivered in conjunction with applied electrical energy.

In general, the methods and apparatuses described herein use an external force in order to make a close contact between cells and the nanostraws. The external force can be a pressure, applying an electric and/or magnetic field, controlling osmotic and/or concentration gradients, use of surface interactions and/or species-species interactions, physical inducement such as centrifugal, flow, shear effects, and/or mechanical compression. Once the cells are in contact with the nanostraws, the cargo can be administered into the cells in any suitable way, including but not limited to diffusion through the nanostraws due to a concentration gradient, by an electric and/or magnetic field, by pressure, by osmotic gradient, by surface interactions and/or species-species interactions, by physical inducement such as centrifugal flow, and/or shear effects.

The examples provided herein for using an external force to enable delivery of molecules into non-adherent cells may be provided in a microfluidic embodiment.

In some variations, force may be applied by centrifugation. Centrifugation can be used to make cells in a suspension come in contact with nanostraws and allow for intracellular delivery of biologically relevant molecules into the intracellular space. For this method, centrifugation may be performed when the cells are in a container incorporating a nanostraw membrane. Once the container with the cells is centrifuged, the cells may be pelleted onto the nanostraws, allowing for intracellular delivery.

FIGS. 1A-1C schematically illustrate the application of force to suspended (non-adherent) tissue, e.g., by centrifugation, onto nanostraws to deliver material into the tissue (e.g., cells). In this example, the nanostraw membrane is fixed to the bottom of a container holding the cells in suspension. During the application of force (e.g., via centrifugation), the cells are pelleted down onto the nanostraws enabling delivery of molecules. The cargo can be delivered into the cells, either during the application of the force driving the cells onto the nanostraws, or just afterwards, when the cells are still in contact with the nanostraws. After a certain time, in the absence of additional force driving the cells onto the nanostraws, the cells can leave the nanostraws and go back into solution again, thereby setting an upper limit to how long one can wait after the centrifugation before the cargo has to be delivered. This upper time limit may be cell specific.

In any of the variations described herein, a binding agent may be used to bind the non-adherent tissue to the nanostraws. The binding agent may be cell-specific or general. For example, an antibody directed to an antigen present on the tissue (e.g., cell surface) may be bound to the nanostraws and/or the membrane from which the nanostraws extend. The binding agent (e.g., antibody) may help capture the tissue for contact with the nanostraws.

In any of the apparatuses and methods described herein, force can be applied to remove the cells from the nanostraws upon demand, including the use of centrifugal force, fluid flow, mechanical force (e.g., retracting the nanostraws, etc.), etc. In some variations one or more chemical and/or enzymatic agents may also or alternatively be used to remove the cells. For example, trypsin, collagenase, and/or other agents may be used to remove the tissue (e.g., cells) from the nanostraws. These agents may be particularly useful when a binding agent, such as an antibody, has been used to secure the tissue to the nanostraws.

For example, described herein are methods of delivering a biologically relevant cargo into non-adherent cells. These methods may include: applying a force to drive a suspension of cells into contact with a plurality of nanostraws, wherein the plurality of nanostraws extend through a substrate and a distance beyond the substrate that is between 2 nm and 50 µm, further wherein the plurality of nanostraws are hollow and have an inner diameter of between 5 nm-1500 nm; and driving the cargo from the nanostraws into an intracellular volume of the cells so that at least some (e.g., 20%, 25%, 30%, 35%, etc.) of the cells take up the biologically relevant cargo.

As used herein, the cells may take up the cargo by receiving the cargo into the intracellular space, including, but not limited to translocation of cargo into subregions of the intracellular space (e.g., the nucleus). Further, taking up cargo may include getting the cargo into the intracellular compartment above a predetermined threshold (e.g., a detectable level, including a level above background).

The force may be applied in any appropriate manner, including by moving the nanostraws to contact the cells, and/or centrifuging the suspension of cells to drive the cells into contact with the plurality of nanostraws. In some variations, the method includes incorporating magnetic particles on or in the cells, and applying force comprises applying a magnetic field to drive the suspension of cells into contact with the plurality of nanostraws.

In any of these variations, driving the cargo may include applying a pulsed electrical field. The cargo may be one or more of: nucleic acids or proteins.

Any of these methods may also include separating the cells from the nanostraws; for example, separating the cells from the nanostraws may comprise flowing a solution over the cells; and/or reversing the force applied to drive the suspension of cells into contact with the nanostraws.

In general, these methods may be performed in vitro.

The nanostraws may be in fluidic communication with a fluidic passage connected to a reservoir of biologically relevant cargo. The suspension of cells may comprise plant cells. The substrate may be a porous structure.

For example, a method of delivering a biologically relevant cargo into non-adherent cells may include: applying a force to drive a suspension of cells into contact with a plurality of nanostraws, wherein the plurality of nanostraws extend through a porous structure and a distance beyond the porous structure that is between 2 nm and 50 µm, further wherein the plurality of nanostraws are hollow and have an inner diameter of between 5 nm-1500 nm; applying a pulsed electrical field to drive the cargo from the nanostraws into an intracellular volume of the cells so that at least 25% of the cells take up the biologically relevant cargo; and separating the cells from the nanostraws.

Also described herein are apparatuses for performing any of the methods described herein. For example, an apparatus for delivering a biologically relevant cargo into non-adherent cells may include: a first flow path, wherein the first flow path is configured to receive a suspension of cells; a deflectable substrate along a lateral side of the first flow path; a plurality of nanostraws extending through the deflectable substrate and into the first flow path, wherein the plurality of nanostraws extend from the flexible substrate, further wherein the plurality of nanostraws are hollow and have an inner diameter of between 5 nm-1500 nm; a reservoir in fluid communication with an inside of the plurality of nanostraws, the reservoir configured to hold the biologically relevant cargo; wherein the deflectable substrate is configured to deflect between a first position and a second position, further wherein the plurality of nanostraws extend further into the first flow path in the second position than in the first position to at least partially occlude the first flow path so that non-adherent cell in the flow path communicate with one or more of the plurality of nanostraws.

The apparatus may also include a pair of electrodes on opposite sides of the first flow path configured to apply an electrical field between the reservoir and the first flow path. These electrode may be configured (sized, positioned, located, etc.) to apply an electrical field between the reservoir and the first flow path when the deflectable substrate is in the second position. The apparatus reservoir may be configured as a second fluidic channel through which the biologically relevant cargo flows.

The first flow path may comprise an inlet at a first end and an outlet at a second end, and may extend between these two. The deflectable substrate may comprises a porous structure. The plurality of nanostraws may extend between 2 nm and 50 μm from the substrate. The deflectable substrate may be configured to transition from the first position to the second position based on the pressure in the reservoir.

Any of these apparatuses may be configured a cartridge.

For example, an apparatus for delivering a biologically relevant cargo into non-adherent cells may include: a first flow path having an inlet port and an outlet port, wherein the first flow path is configured to receive a suspension of cells; a deflectable substrate along a lateral side of the first flow path; a plurality of nanostraws extending through the deflectable substrate and into the first flow path, wherein the plurality of nanostraws extend between 2 nm and 50 μm from the substrate, further wherein the plurality of nanostraws are hollow and have an inner diameter of between 5 nm-1500 nm; a reservoir in fluid communication with an inside of the plurality of nanostraws, the reservoir configured to hold the biologically relevant cargo; wherein the deflectable substrate is configured to deflect between a first position and a second position, further wherein the plurality of nanostraws extend further into the first flow path in the second position than in the first position to at least partially occlude the first flow path so that non-adherent cell in the flow path communicate with one or more of the plurality of nanostraws; and a pair of electrodes on opposite sides of the first flow path configured to apply an electrical field between the reservoir and the first flow path.

BRIEF DESCRIPTION OF THE DRAWINGS

The novel features of the apparatuses and methods are set forth with particularity in the claims that follow. A better understanding of the features and advantages will be obtained by reference to the following detailed description that sets forth illustrative embodiments, in which the principles of the invention are utilized, and the accompanying drawings of which:

FIGS. 1A-1C show a schematic of a side view of a container incorporating a nanostraw membrane in the bottom, filled with a suspension of tissue (cells), as shown in FIG. 1A. Under an external force, such as centrifugation, non-adherent cells can be used to put the cells in close contact with the nanostraws, as shown in FIG. 1B. While the cells are in contact with the nanostraws, and the bottom of the nanostraws are in contact with a cargo solution within the nanostraws, cargo can be delivered into the cells, as shown in FIG. 1C. Schematic is not to scale.

FIGS. 2A-2B show delivery of DNA oligomer into human induced pluripotent stem cells (iPSCs) in the flotation stage though nanostraws in which force was applied by centrifugation. The differential image contrast, in FIG. 2A, shows the total number of cells. The green channel, in FIG. 2B, shows the cells in which the oligomer was delivered. The cells were centrifuged at 300 g for 5 min onto 100 nm diameter nanostraws with 1.2 μm length. The delivery was enhanced by applying 200 μs long 20 V voltage pulses, with 40 Hz frequency for 80 s, after the centrifugation.

FIGS. 3A-3D illustrate delivery of DNA oligomer into Jurkat cells. FIG. 3A shows Hoechst staining, illustrating the total number of cells by staining the nuclei. The green channel in FIG. 3B shows the cells in which the oligomer was delivered. The cells in this example were centrifuged at 300 g for 5 min onto 200 nm diameter nanostraws with 1.2 μm length. The delivery was enhanced by applying a train of 200 μs long 20 V voltage pulses, with 40 Hz frequency for 40 s, after the centrifugation. The delivery could be repeated for another 40 s. A second delivery resulted in similar delivery efficiencies (percentage of cells that received the cargo), as shown in FIG. 3C, but with close to a doubling of the fluorescence intensity in the cells, as shown in FIG. 3D.

FIGS. 4A-4B are cytograms showing eGFP-plasmid expression, in FIG. 4A, and Cas9 ribonucleoprotein complex delivery, in FIG. 4B, into Jurkat cells. In a, the expression of eGFP plasmid three days after nanostraw mediated delivery is shown. More than about 30% of the cells expressed the plasmid. In FIG. 4B, a GFP-tagged Cas9 ribonucloeprotein complex was delivered into Jurkat cells using nanostraws with more than 25% efficiency. The cells were centrifuged at 300 g for 5 min onto 200 nm diameter nanostraws with 1.2 μm length. The delivery was enhanced by applying a train of 200 μs long 20 V voltage pulses, with 40 Hz frequency for 40 s, after the centrifugation. Cells which got PBS delivered to them were used to gate the cytograms.

As mentioned, any tissue or cell type, including plant cells, may be used with the methods and apparatuses described herein. FIGS. 5A-5C show nanostraw-centrifugation (in which cells in suspension were driven into contact with the tips of a plurality of nanostraws by centrifugation) mediated delivery into plant cells. FIG. 5A shows deliver of propidium iodide (PI) into Havana tobacco protoplast cells. FIG. 5B shows delivery of PI into Havana tobacco cells in suspension. Nuclear staining was visible by a blue color using Hoechst, red shows the cells that received PI. FIG. 5C shows the delivery and expression of TD18 (RFP) plasmid into ST1 Switchgrass protoplast cells. The background shows the total number of cells, the red overlay shows a cell expressing the RFP after successful delivery. The cells were centrifuged at 150-200 g for 10 min onto 100 nm diameter nanostraws with about 2 um length. The delivery was enhanced by applying a train of 200 μs long 20 V voltage pulses, with 40 Hz frequency for 40 s, after the centrifugation.

Other plant cells may be used, including cells of protoplast, meristem, pollen, callus, suspension cells containing cell walls), plant embryos, etc. As mentioned, even cells, such as plant cells, having a cell wall may be treated as described herein.

FIGS. 6A-6C show a side schematic view of an exemplary apparatus in which pressure (e.g., mechanical force) is used to press the cells onto the nanostraws by moving the nanostraws onto the cells. This variation may be referred to as a "French press" apparatus.

FIGS. 6D-6F show another variation of an exemplary apparatus similar to that shown schematically in FIGS. 6A-6C. In FIG. 6D, the bottom of the chamber may include a plurality of openings or pores through which fluid may be driven; these opening may be too small to allow the cells to allow passage of the cells, but the flow of fluid out of the chamber may drive the cells against the bottom allowing contact with the nanostraws, as shown in FIG. 6E, for delivery of cargo, as shown in FIG. 6F.

FIGS. 7A-7D show mouse embryos after a DNA oligomer tagged with a red fluorescent molecule was delivered to them. The embryo shown in FIG. 7A (using bright field microscopy) was pressed by adding 150 μl of oil on top of the cargo. The protective zona pellucida (ZP) can be seen to be intact and surrounding the oocyte. When observing the fluorescence, in FIG. 7B, it is apparent that the oligomer goes into the perivitelline space (between ZP and oocyte) as well as into satellite cells. However, no oligo can be seen inside the oocyte. The embryo in FIG. 7C was pressed using 300 µl of oil on top of the cargo. That pressure is enough to enable the straws to penetrate into the oocyte itself to deliver the oligomer, as is evidenced by the red fluorescence inside the oocyte, shown in FIG. 7D. The embryos were pressed by 200 nm diameter nanostraws with about 1.2 um length. 100 ul of DNA oligomer tagged with a red fluorescent molecule, diluted in 0.1× PBS was loaded as the cargo solution. 150 or 300 µl of mineral oil was added to the embryos in FIGS. 7A-7B and FIGS. 7C-7D, respectively, as extra weight was used to press the nanostraws onto the embryos. The delivery was enhanced by applying a train of 200 µs long 20 V voltage pulses, with 40 Hz frequency for 80 s. A spacer of 50 µm height was used for both deliveries to ensure that the embryos were not squeezed too much. The yellow line in FIG. 7A outlines the ZP.

Figure 8A:
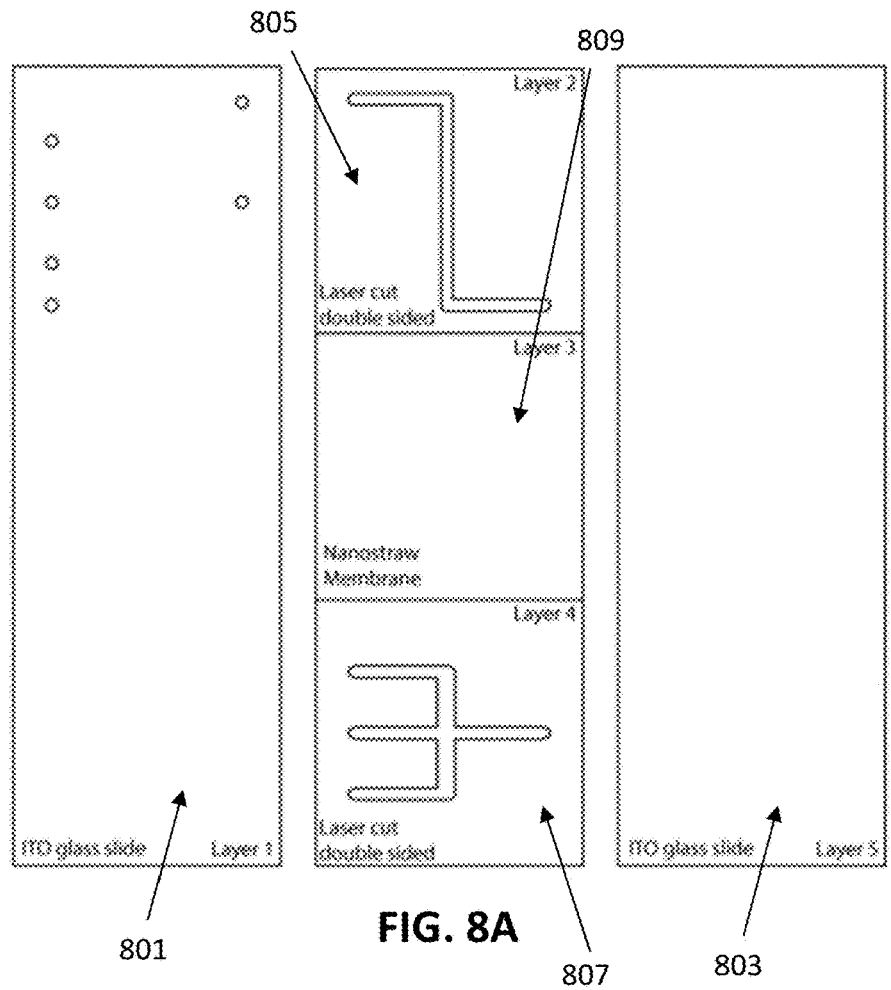
Figure 8B:
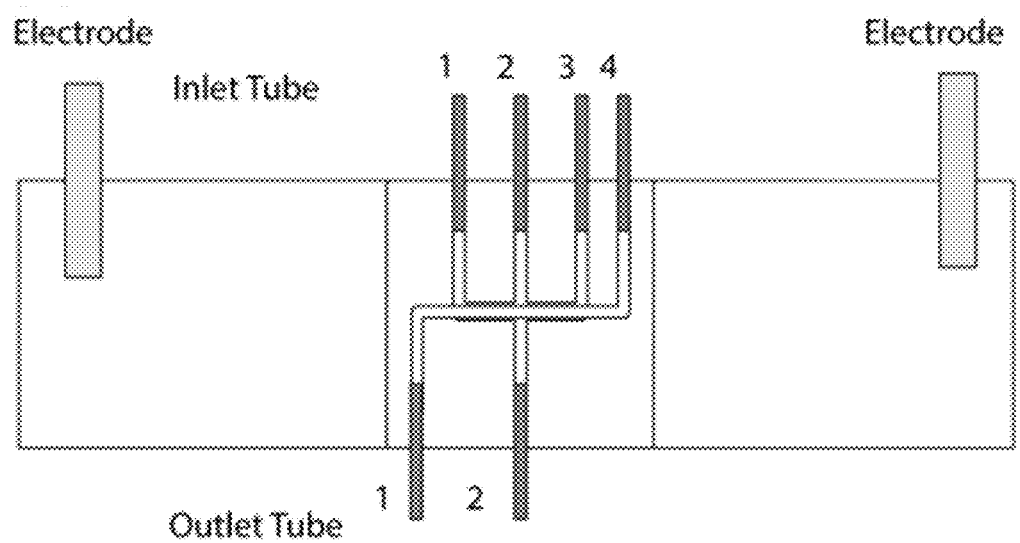

FIGS. 8A-8B show a layout of one example of a flow-through device for high throughput delivery that performs the methods described herein. FIG. 8A shows a top view of components that may make a flow-through device.

Figure 9A:
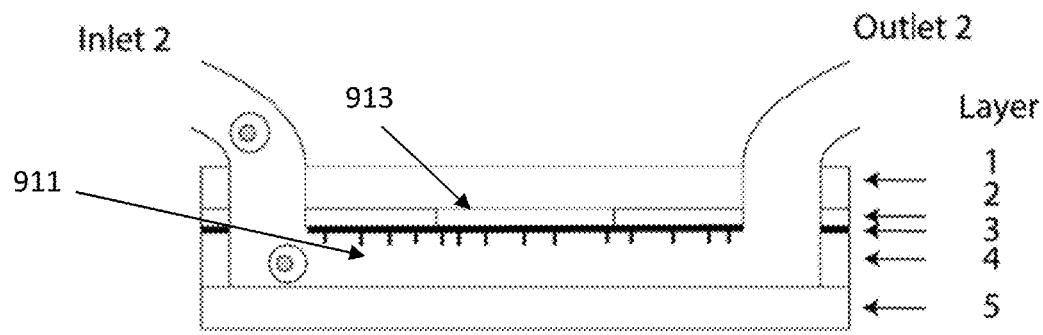
Figure 9B:
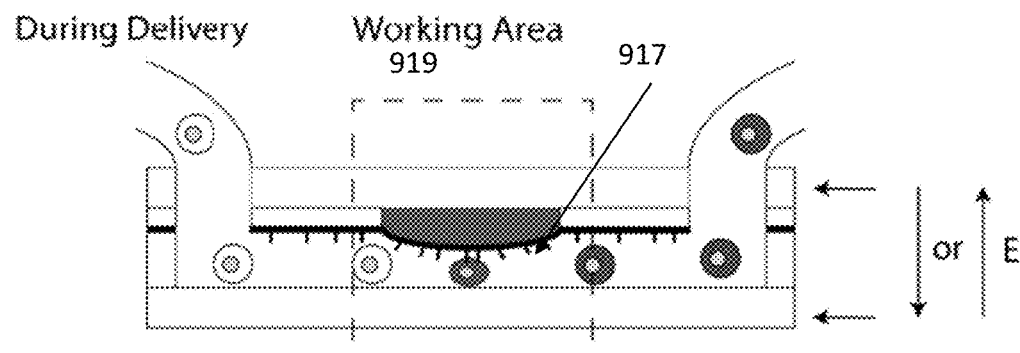

FIGS. 9A-9B show another example of a flow-through device in use. In FIG. 9A, a side view schematically shows the layout of the exemplary assembled device. Cells are injected through inlet 2, passing by underneath the nanostraws, and are collected at outlet 2. In FIG. 9B, the same side view shows the device during delivery of a cargo into cells flowing through the device. In FIG. 9B, the increased pressure in the cargo reservoir makes the nanostraw membrane bend, thereby coming in contact with the cells, allowing for intracellular access.

Figure 10A:
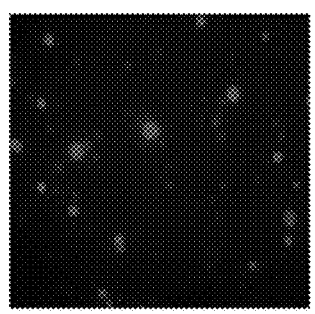
Figure 10B:
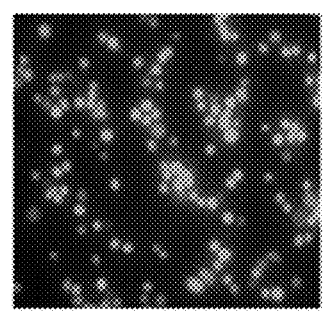
Figure 10C:
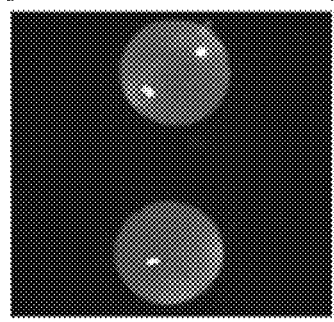

FIGS. 10A-10C illustrate an example of cells transfected with a flow-through device such as that shown in FIG. 9A-9B. In FIG. 10A, HEK293 cells in the floatation stage after delivery of dextran blue as schematically illustrated in FIGS. 9A-9B. FIG. 10B shows Calcein AM staining having a high cell viability after delivery. FIG. 10C shows delivery of propidium iodide (PI) dye to mouse oocytes (red channel).

Figure 11:
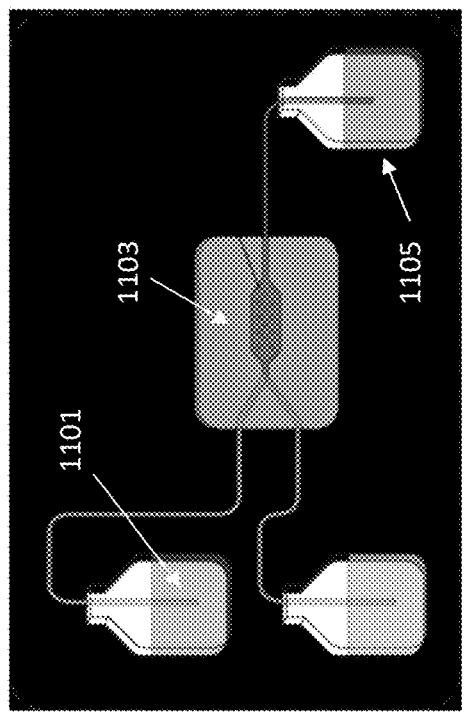

FIG. 11 is a schematic of a closed loop system for nanostraw transfection. In this example, cells flow into the nanostraw device together with the desired cargo. The cargo is delivered through the nanostraws and into the cells, after which they are transported to a sterile cell holding flask. After completion, the flask can be removed for use.

Figure 12A:
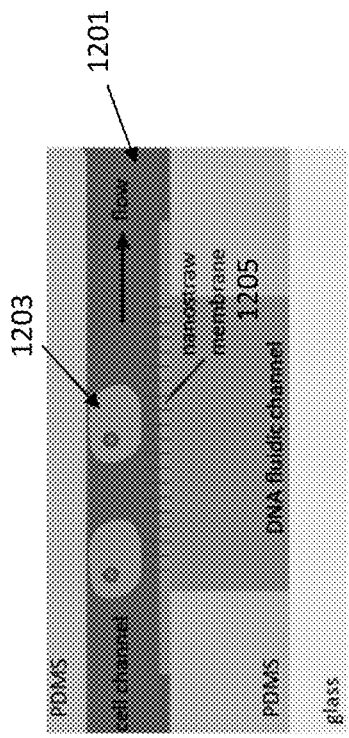
Figure 12B:
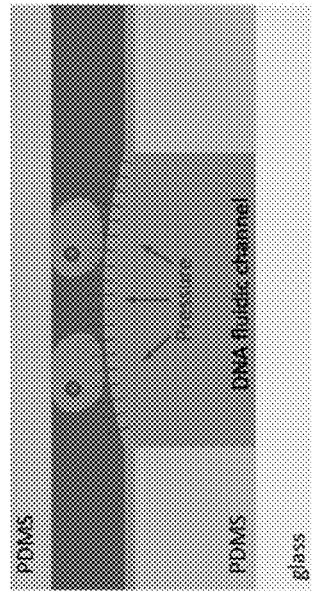
Figure 12C:
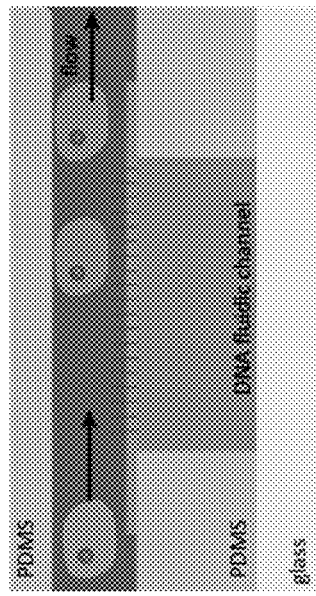

FIGS. 12A-12C illustrate another example of a flow-through device for transfecting non-adherent tissue using nanostraws, similar to that shown in FIGS. 9A-9B. In this example of a nanostraw delivery system, cells are flowed into the transfection chamber, as shown in FIG. 12A. In FIG. 12B, pressure is applied to the cargo channel, pressing the nanostraws into the cell. The amount of applied pressure may be controlled by the flow rate. As shown in FIG. 12C, once the pressure is released, cells may be transported to a collection container.

Figure 13:
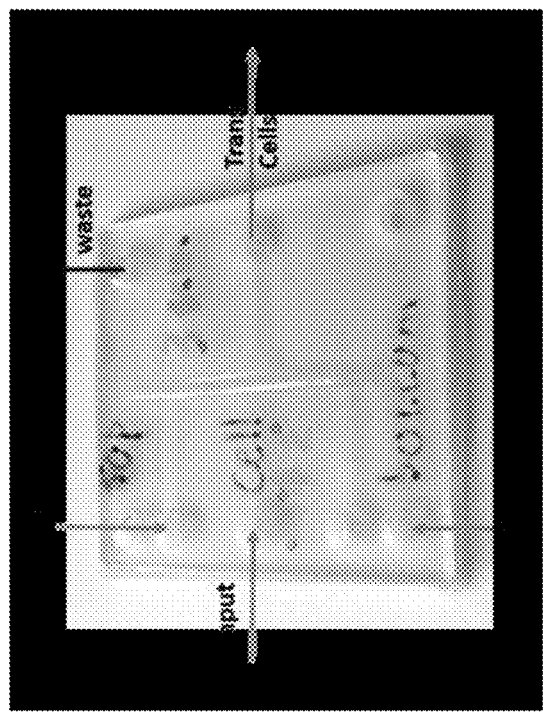

FIG. 13 is an example of a prototype flow-through apparatus.

Figures 14A, 14B, 14C, 14D, 14E, 14F:
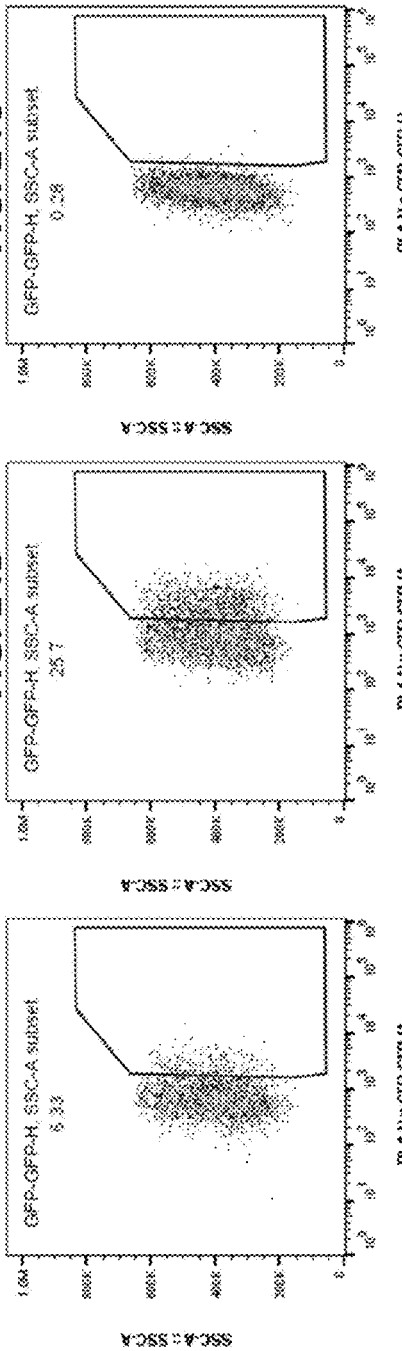

FIGS. 14A-14F show cytograms of GFP-tagged CAS9 ribonucleoprotein complex delivery into Jurkat cells using a wide range of salt concentrations for the buffer that the CAS9 was diluted in; transfection is performed using the methods and apparatuses described herein, applying force by centrifugation onto the nanostraws. Salt concentrations are: DDH20 (FIG. 14A), 0.1×PBS (FIG. 14B), 1×PBS (FIG. 14C), 2×PBS (FIG. 14D). FIG. 14E shows cells which were delivered 1×PBS (no CAS9). FIG. 14F shows untreated cells. The cells were centrifuged at 300 g for 5 min onto 200 nm diameter nanostraws with 1.2 µm length. The delivery was enhanced by applying a train of 200 µs long 20 V voltage pulses, with 40 Hz frequency for 120 s, after the centrifugation.

Figure 15A:
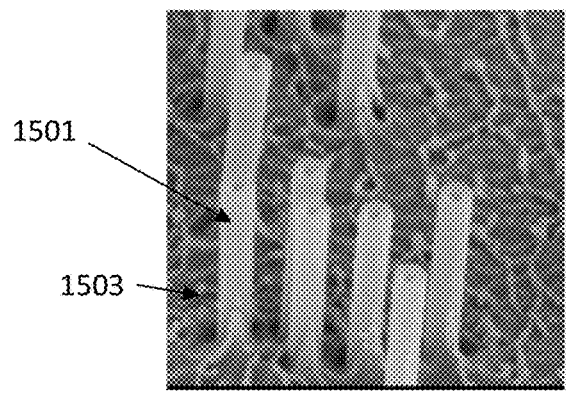
Figure 15B:
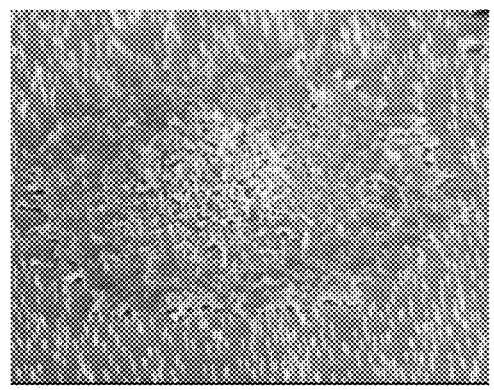

FIGS. 15A-15F illustrate one example of a substrate from which a plurality of nanostraws extend. FIG. 15A shows an example of an SEM of a substrate from which nanostraws extend. FIG. 15B is an example of an adherent cell (Chinese hamster ovary, CHO, cell) grown and adherent to the substrate with nanostraws. FIGS. 15C-15F illustrate one method of fabricating nanostraws that may be used with any of the apparatuses and methods described herein.

Figure 16A:
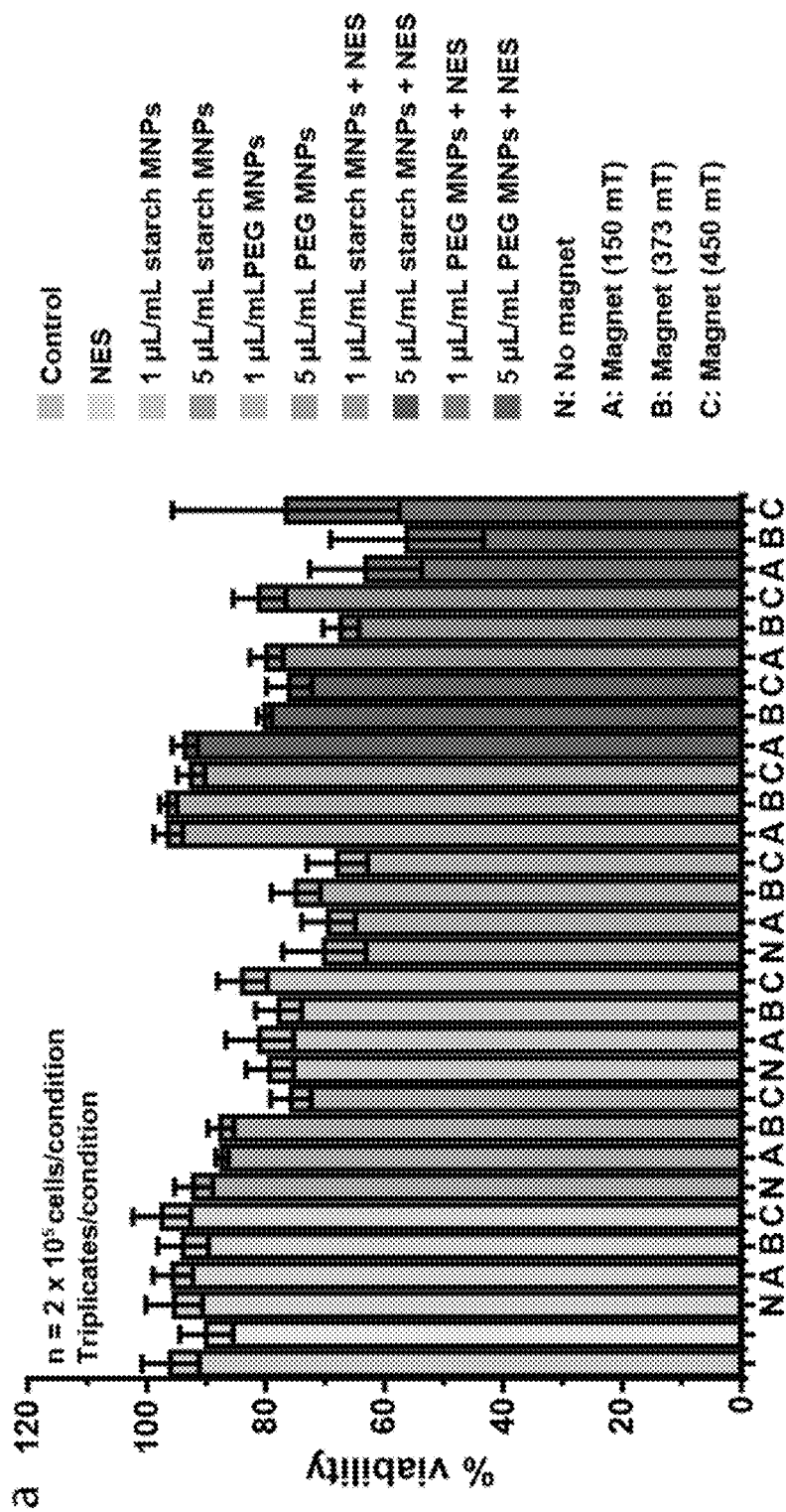
Figure 16B:
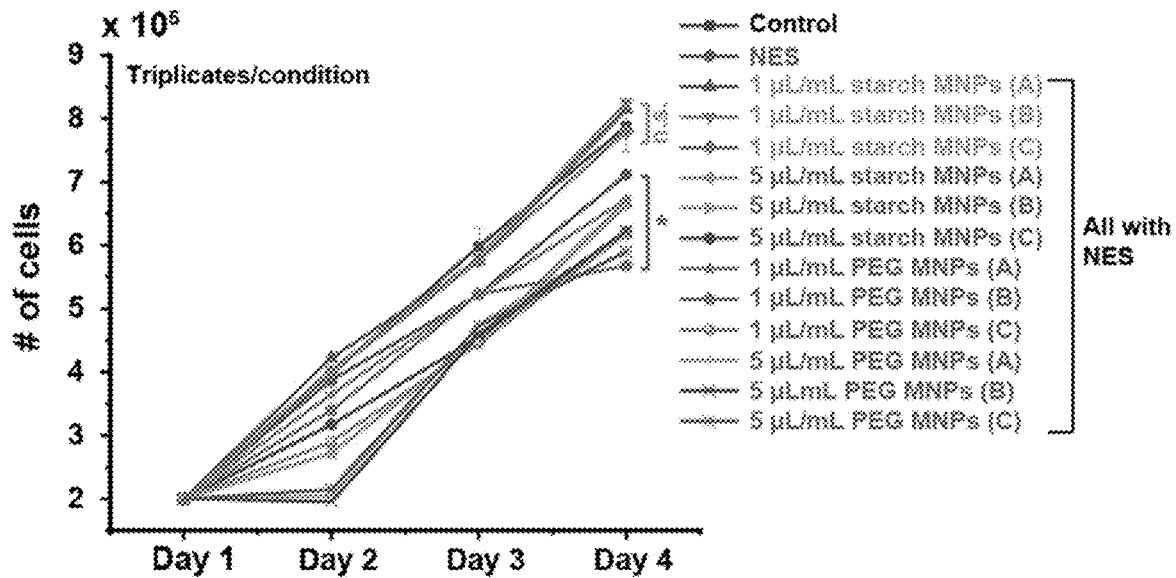
Figure 16C:
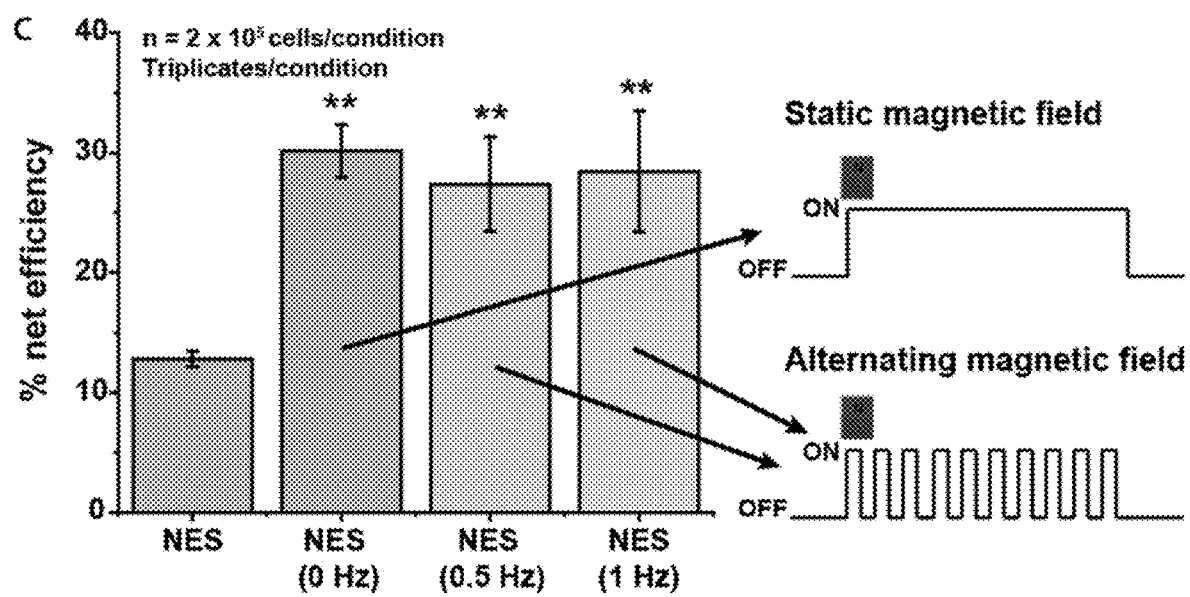
Figure 16D:
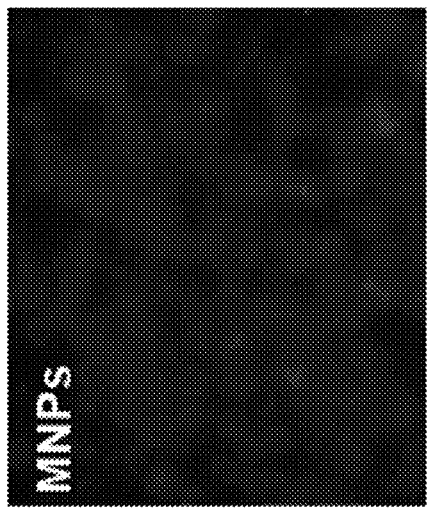
Figure 16E:
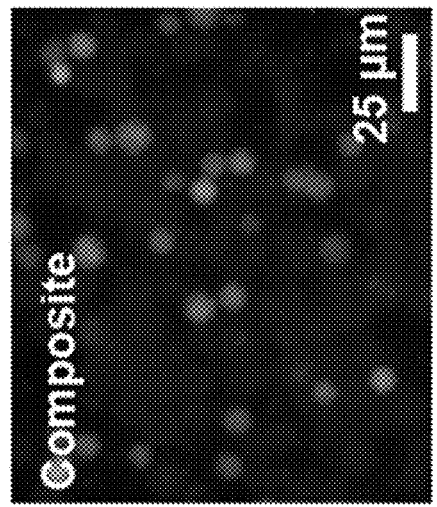
Figure 16F:
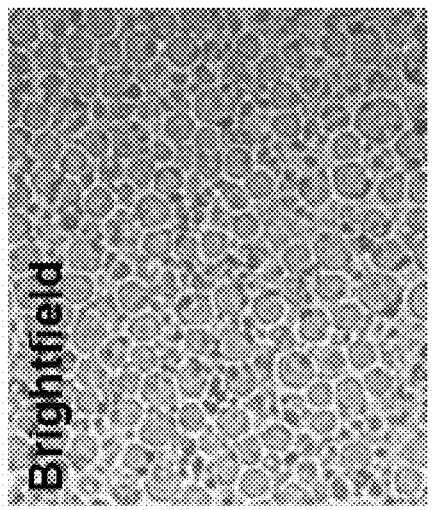
Figure 16G:
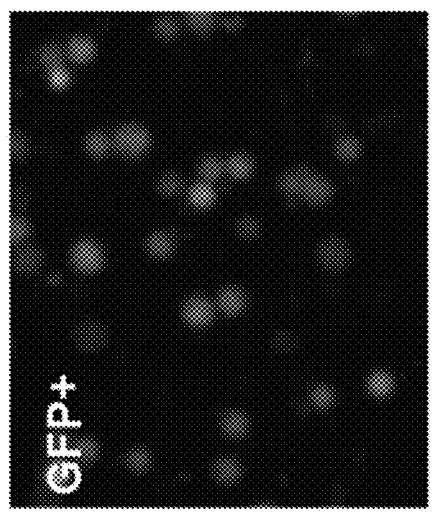

FIG. 16A-16G illustrate the use of magnetic beads to drive non-adherent cells into contact with the open ends of a plurality of nanostraws. FIG. 16A shows the effect of viability on exemplary cells combined with magnetic particles (MNPs). In FIG. 16A, cell viability with either starch- or PEG-coated MNPs in 1 or 5 µL/mL without or with different magnetic field strengths for 24 hr. were monitored. Cell viabilities with 1 µL/mL starch-coated MNPs were similar to control while the other conditions had lower cell viability. FIG. 16B illustrates the proliferation of the cells over 4 days. Treatments with 1 µL/mL starch-coated MNPs did not significantly affect cell proliferation while others, including only NES, delayed cell proliferation. The labels 'A', 'B' and 'C' refer to magnetic field strengths as listed in the legend of FIG. 16A. FIG. 16C illustrates the effect of magneto-mechanical modulation with static magnetic fields, showing a significantly improved net transfection efficiency from 12.8% to about 30%. The use of low-frequency alternating magnetic fields did not result in any significant difference in net transfection efficiencies. In this example, a magnet was placed about 3.6 cm, measured from the center of the magnet, away from the cells, providing $F_{max|mag}$=19.0 pN/cell. FIGS. 16D-16G illustrate one example of magnetic beads used to drive the contact between the ends of nanostraws and the cells. FIG. 16D shows a brightfield image of cells following treatment. FIG. 16E shows the same image, with a florescent marker for MPSs that have been taken up by the cells (the majority of the cells have associated MNPs). FIG. 16F is the same field of view, imaging a marker (green florescent protein) added to the cells as the cargo from the nanostraws, while FIG. 16G is a composite image showing both MNPs and the delivered cargo GFP. The resulting images show an about 30% net transfection efficiency using the magnetic particles *: p<0.05, **: p<0.001. Error bars shown are ±standard mean error.

DETAILED DESCRIPTION

Described herein is use of nanostraws to deliver biologically relevant cargo into non-adherent cells. The methods and the apparatuses (including devices and systems) described herein may apply a force to drive (and in some variations, sustain) contact between the tip of the hollow nanostraws and the cell, so that a biologically relevant cargo can be transferred from a reservoir, through the nanostraws and into the cells.

The force applied may be a mechanical force, e.g., pressing the cells and/or the nanostraws into contact with each other, for example, by moving the nanostraws into the cells and/or using fluid flow (e.g., fluid pressure) to drive cells onto the nanostraws. Alternatively or additionally, the force may be due to centrifugation. Alternatively or additionally, the force may be magnetic, e.g., driving magnetic particles coupled to the cells so that the cells contact the nanostraws. Any of these examples may be combined or used separately.

In any of these methods and apparatuses, a pulsed electrical field may be used to enhance transfer of the biologically relevant cargo from the nanostraws into the cells. The pulsed electromagnetic field may be applied during or after the application of force.

In any of these method and apparatuses the cells may be removed from the nanostraws following transfer of a sufficient amount of cargo.

Any appropriate cargo ("biologically relevant cargo") may be used. In particular, cargo may include nucleotides (e.g., DNA, RNA, including but not limited to double stranded DNA, single stranded DNA, plasmids, mRNA, microRNA, siRNA, etc.), proteins, small molecules, and/or combinations of these. Cargo may also include markers (dyes, florescent agents, etc.) or the like. Cargo may include protein complexes (e.g., proteins having tertiary or quaternary structure, such as protein subunits, enzymes, etc.). In addition, any desired concentration of cargo may be used (e.g., between 1 pg/ml and 1 mg/ml, 1 ng/ml and 1 mg/ml, etc.)

Figure 15C:
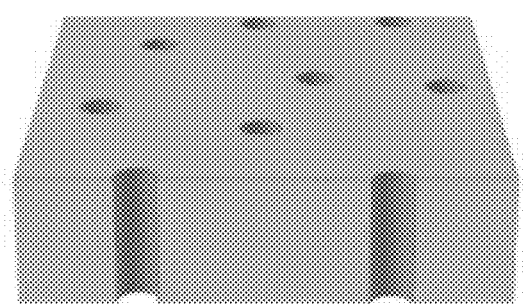
Figure 15D:
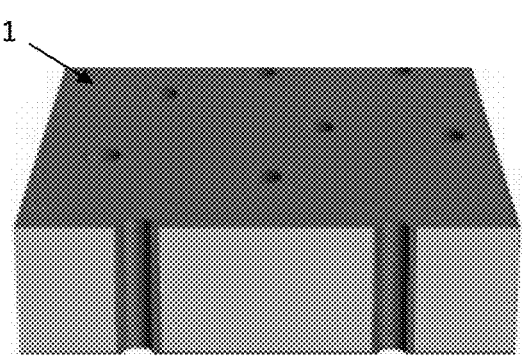
Figure 15E:
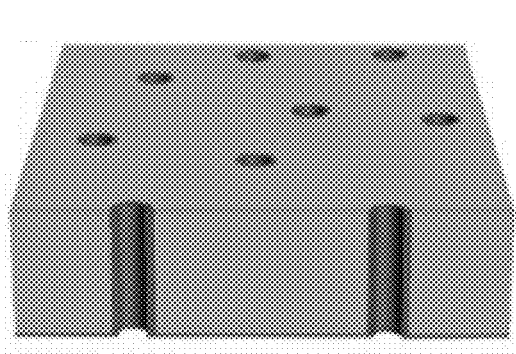
Figure 15F:
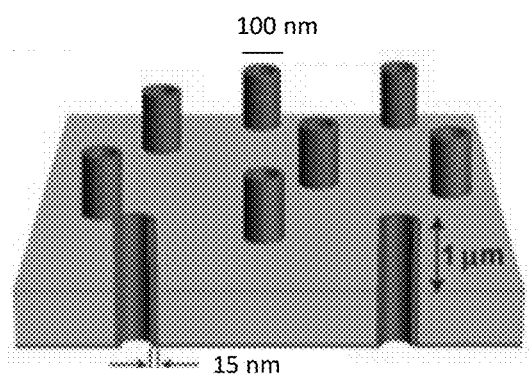

In general, nanostraws are hollow inorganic nanotubes that may be formed from nanoporous polymer films. FIG. 15A illustrates one example of a substrate (a nanoporous substrate) having a plurality of nanostraws 1501 extending through and out of the substrate 1503. These nanostraws can pierce the cell membrane, enabling direct delivery of biological or chemical cargoes through the nanostraws and into the cell. This process avoids biological challenges related to endocytosis and degradation, and is largely agnostic to the cargo type (e.g., DNA, RNA, proteins, and small molecules, etc.). FIG. 15A is an SEM of one example of nanostraws projecting from a substrate. FIG. 15B shows an example of an adherent cell type (e.g., a fibroblast 1508) growing on the substrate and over the nanostraws. FIGS. 15C-15F illustrate schematically one method of fabricating nanostraws. In this example, nanostraws are fabricated starting with track-etched polycarbonate membrane as a template for the nanostraws (FIG. 15C). A range of pore sizes may be used (e.g., between about 20 nm to about 10 μm) and pore densities (e.g., between about $1 \times 10^5$-$1 \times 10^9$ pores/cm$^2$, between about $1 \times 10^6$-$1 \times 10^9$ pores/cm$^2$, between about $1 \times 10^7$-$1 \times 10^9$ pores/cm$^2$, between about $1 \times 10^5$-$1 \times 10^8$ pores/cm$^2$, between about $1 \times 10^6$-$1 \times 10^8$ pores/cm$^2$, between about $1 \times 10^6$-$1 \times 10^7$ pores/cm$^2$, between about $1 \times 10^8$-$1 \times 10^9$ pores/cm$^2$, greater than about $1 \times 10^6$ pores/cm$^2$, greater than about $1 \times 10^7$ pores/cm$^2$, greater than about $1 \times 10^8$ pores/cm$^2$, etc.). A silica or alumina coating 1511 may be deposited on the substrate (e.g., FIG. 15D). Atomic Layer Deposition (ALD) may be performed on all nanoporous membrane surfaces (top, bottom, and inside the pores). The completely isotropic gas-phase nature of the ALD deposition process may yield a highly uniform coating (+/−<5%), typically chosen to be 15-20 nm thick (e.g., FIG. 15E). The alumina on the top surface may be removed with a directional Reactive Ion Etch (RIE) to expose the bare polymer layer underneath, removing the top surface and leaving the coatings in the nanopores undisturbed. Finally, an oxygen plasma etcher may be used to expose the inorganic nanostraws by selectively etching the polymer until the desired nanostraw height is obtained, typically 1-2 μm (FIG. F). The oxygen RIE is highly selective for polycarbonate, ensuring that the alumina nanostraws are not degraded as the straws are revealed. The nanostraw dimensions may be independently controllable through adjustments to the track-etched membrane properties (straw diameter and density), ALD alumina thickness (straw wall thickness), and etch time (nanostraw height).

Although the example above refers to alumina and silica nanostraw materials, other materials may be used, including hafnia.

FIGS. 1A-1C illustrate the general method described herein for delivering a biologically relevant cargo into non-adherent cells. In FIG. 1A, the solution or suspension of non-adherent cells 101 is shown above a substrate 103 through which a plurality of nanostraws 105 extend (not shown to scale). A force 109 is applied to drive a suspension of cells into contact with a plurality of nanostraws, as shown in FIG. 9B. The cells therefore contact the open distal tips of the plurality of nanostraws extending through a substrate; the nanostraws all extend a distance beyond the substrate (e.g., between 1 nm and 100 μm, between 2 nm and 50 μm, greater than 1 nm, greater than 2 nm, greater than 5 nm, etc.). As mentioned, the nanostraws further wherein the plurality of nanostraws are hollow (and may have an inner diameter, e.g., between about 1 nm-1750 nm, between about 5 nm-1500 nm, etc.). In any of the methods described herein an electric field (e.g., a pulsed electric field) may be applied to help drive the cargo into the cells once they've made contact with the nanostraws. After an appropriate time (e.g., one second, 10 seconds, 30 seconds, 45 seconds, one minute, 2 minutes, 3 minutes, 5 minutes, 10 minutes, etc.) the cargo is transferred to all or some (e.g., greater than 20%, greater than 25%, greater than 30%, greater than 35%, greater than 40%, greater than 50%, greater than 60%, greater than 70%, greater than 80%, greater than 90%, etc.) of the cells have taken up the cargo, as shown schematically in FIG. 1C. Thereafter, the cells may be separated from the nanostraws, and placed back into solution. They may then be further processed.

For example, FIGS. 2A-2B illustrate one example in which centrifugation was used to apply force to drive contact between non-adherent cells and a plurality of nanostraws. In this example, human induced pluripotent stem cells (hiPSCs) in the floatation stage were delivered using the nanostraw-centrifugation method. FIGS. 2A-2B show that this method can be used to deliver DNA oligomers tagged with a green fluorescent molecule. hiPSCs were placed in a container incorporating a nanostraw membrane in the bottom. Instead of allowing the cells to sediment and adhere to the surface, they were centrifuged down at 300 g for 5 min. Once centrifuged, an external electric field was applied to assist in delivery of the tagged oligomer (the cargo) from the nanostraws. In FIG. 2A, the differential image contrast (DIC), shows the total number of cells, whereas the green channel (FIG. 2B) show the cells in which the DNA oligomer was delivered. It can be seen that most of the cells received the DNA oligomer. From this, we can conclude that this method can be used to deliver molecules into adherent cells in the flotation stage. This method greatly increases the throughput of nanostraw delivery into adherent cell types since it removes the conventional overnight cell plating while maintaining high efficiency delivery.

In another example of this method, Jurkat cells were centrifuged onto nanostraws for efficient delivery of molecular cargo. Jurkat is a human T-cell lymphoma cell line that bear many resemblances to T-cells. Molecular delivery into T-cells, and T-cell mimics is a key step for implementing immunotherapeutic approaches such as chimeric antigen receptor (CAR) T-cells. Jurkat cells grow in suspension and it has not previously been possible to deliver to using nanostraws. FIGS. 3A-3D show the result of centrifuging these cells down onto nanostraws, indicating an efficient delivery of molecular cargo can be performed by this method for the first time using nanostraws. The Jurkat cells were placed in a container incorporating a nanostraw membrane in the bottom. The cells were centrifuged at 300 g for 5 min, after which a DNA oligomer tagged with a green fluorescent dye was delivered for a total of 40 s (enhanced by applying short voltage pulses). By studying the number of green cells (indicating cells which got the oligomer delivered) vs. the total number of cells as visualized by staining the nuclei using Hoechst 33342, it was found that more than 90% of the cell received the cargo by this method. The Hoechst staining showed more than 95% cell viability as determined by the lack of chromatin condensation.

Increased delivery time using the same cargo solution also enabled dosage controlled delivery. Doubling of the delivery time did not significantly alter the percentage of cells that got the cargo, as shown in FIG. 3C, but it did result in a close to doubling of the amount of delivered cargo, as shown in FIG. 3D. In FIG. 3D the fluorescence intensity of the oligomer inside the cells was determined, showing that cells having twice the delivery time in contact with the nanostraw under pulsed electric field received nearly twice the cargo.

The use of force, in this example, centrifugation, to drive non-adherent immune cells onto nanostraws can be used for efficient, dosage controlled, delivery of cargo with high cell viability, thereby enabling efficient gene editing of immune cells for immunotherapeutic applications.

The coupled use of force (e.g., centrifugation) to drive non-adherent cells (in suspension) onto nanostraws may be used to deliver cargo much larger than DNA oligomers. In FIG. 4A, a cytogram shows the expression of eGFP-plasmid in more than 30% of the Jurkat cells in which it was delivered. The delivery was performed similar to the oligomer deliver in the Jurkats by centrifuging the cells down onto nanostraws at 300 g for 5 min. The delivery was enhanced by the addition of a pulsed electric field. The cytogram was obtained three days after the nanostraw delivery, showing that the cells proliferated without problems after the nanostraw delivery. FIG. 4B shows the delivery of a GFP-tagged Cas9 ribonucleoprotein complex into Jurkat cells. The Cas9 protein is highly relevant for a number of gene editing applications, including immunotherapy. The achieved delivery efficiency of more than 25% shows that nanostraw mediated delivery is a viable route for targeted gene editing in hard to transfect cells. The ability to deliver the protein directly and not having to rely on expression of DNA or mRNA inside the cells holds promises for faster and more reliable gene editing.

As mentioned above, plant cells can be pierced by nanostraws for intracellular delivery using the methods and apparatuses described herein. Plant cells, unlike animal, e.g., mammalian cells, may include a several-micrometer thick cell wall that surrounds the cellular membrane. The cell wall is made from polysaccharide and provides, among other things, mechanical support. Delivery of cargo beyond the wall is very challenging, but may be performed using the methods and apparatuses described herein. In some instances, the cell wall can be removed using different enzymes in order to produce a so-called protoplast culture.

Nanostraws can deliver non-cell permeable molecules into both plant protoplasts and cells in suspension. In the example shown in FIG. 5A, a protoplast culture of Havana tobacco cells was placed in a container incorporating a nanostraw membrane in the bottom. The cells were centrifuged onto the nanostraws at 150 g for 10 min followed by voltage assisted delivery of a non-cell permeable stain, propidium iodide (PI). The red cells have received the PI stain and by comparing the PI to nuclear staining using Hoechst, blue color, we could deduce that more than 90% of the cells received the PI. For tobacco cells in suspension (i.e. with a full cell wall), FIG. 5B, the PI delivery had a lower efficiency which may be partly attributed to the 3-dimensional agglomeration that the suspension cells present. Even so, PI can clearly be delivered to some of the cells. FIG. 5C shows expression of a nanostraw-centrifugation delivered RFP-plasmid in switchgrass protoplast culture. These results show that the presented method can be used to gain intracellular access into plant cells both with and without a cell wall.

For nanostraws of diameters 10-1000 nm and lengths of 0.1-25 m, centrifugation speeds from 1-100,000 g can be used. Different centrifugation speeds may be used depending on the cell type, since a physical penetration may be dependent on cell membrane failure stress, cell size, and density. For example, most mammalian cells may be driven onto a nanostraw by centrifugation using 100-3000 g centrifugation for 2-20 min. Optimized at 300 g for 5 min.

Similarly, in some variations, T-cells may be driven onto the nanostraws as described herein, using a centrifugation speed of about 200-2000 g for 2-20 min. This may be optimized to approximately 750 g for 5 min. The need for higher speeds is explained by their smaller size. For example, plant cells in suspension and protoplasted plant cells have been used. Preliminary work suggests that the method include driving the plant cells onto a nanostraw using approximately 1-1000 g for 2-20 min, which may be optimized at 200 g for 5 min. Other cell types (e.g., yeast cells) may use other parameters for applying force by centrifugation, e.g., spinning down onto the nanostraws at about 1000-6000 g for 5-60 min. Embryos may be applied by centrifuging at between 1-1500 g for 0.1-30 min. The larger size of embryos allow delivery at lower centrifugation speeds. Bacteria may be driven onto a plurality of nanostraws using, e.g., 1500-10,000 g for 5-60 min. The small size, and thick cell wall of bacteria may take a higher centrifugation speeds.

After the centrifugation, the cargo may be delivered before the cells go off in suspension again, generally before 30 min. Some cell types, such as large plant cells, can wait longer whereas some cell types, such as small T-cells, may be delivered to within 5 min.

In general, the buffer in which the cells are suspended during the centrifugation can be chosen to be any kind of liquid that will not lyse the cells. More viscous materials can be used to stabilize the cells on the nanostraws for a longer time and reduce the risk of cells going off into solution before the delivery has been performed. For bacteria, pure water is not recommended since it can cause aggregation of the bacteria.

In some variations, mechanical force may be applied so that nanostraws can be pressed onto cells in order to gain intracellular access, the so called "French press" embodiment. In this example, illustrated in FIGS. 6A-6C and 6D-6E, a container incorporating a nanostraw membrane 601 in the bottom is filled with a cargo solution 605, FIG. 6A. Unlike the centrifugation-based method described above, since the nanostraws extend out from the container, facing down, cells are placed on a surface surrounded by a thin spacer whose height is chosen to match the height of the cells of interest. The nanostraw container 601 is placed on top of the cells such as to put the nanostraws and the cells in contact. If needed, extra pressure can be applied by adding another fluid on top of the cargo solution. Once a suitable pressure is applied, cargo can be delivered into the cells, including applying the transfer charge (e.g., applying a pulsed electric field).

When mechanical force is used to drive the cells into the nanostraws in the "French press" variation, cells may be dispersed on a flat surface surrounded by walls of a defined height. A container consisting of a porous membrane 601 incorporating nanostraws 603 may be extended downwards placed on top of the cells 607. The container may hold the cargo of interest 605 with the option of an extra weight e.g. oil 609 that can provide extra pressure. When pushed towards the cells (as shown in FIG. 6B), the cells will be squeezed, resulting in the nanostraws coming in close proximity to the cells. The nanostraws can then be used for delivery of a cargo into the cells, either by diffusion due to a concentration gradient or by adding external driving forces such as an electric field, centrifugation, liquid flow, etc.

Another variations is shown in FIGS. 6D-6F. In this example, as above, there is a receptacle for suspended, non-adherent cells 617 and the substrate with nanostraws may be moved into the receptacle; this may displace some of the fluid, which may pass through the base. The base in this example includes openings 621 (channels, pores, etc.) that may pass the fluid (as shown in FIG. 6E) when the substrate and nanostraws are lowered into the base, and may allow the substrate and nanostraws to drive the cells against the base so that they may be supported while the nanostraws contact them in order to pass cargo into the cells.

Mouse embryos can be accessed by pressing the nanostraws onto them. Embryos present a challenging task for nanostraw delivery mainly due to the several micrometer thick zona pellucida (ZP) that surrounds the entire oocyte. Many bio-relevant molecules, such as gene editing tools, need to be delivered into the oocyte and reliable access to it is therefore of high interest.

Figures 7A, 7B, 7C, 7D:
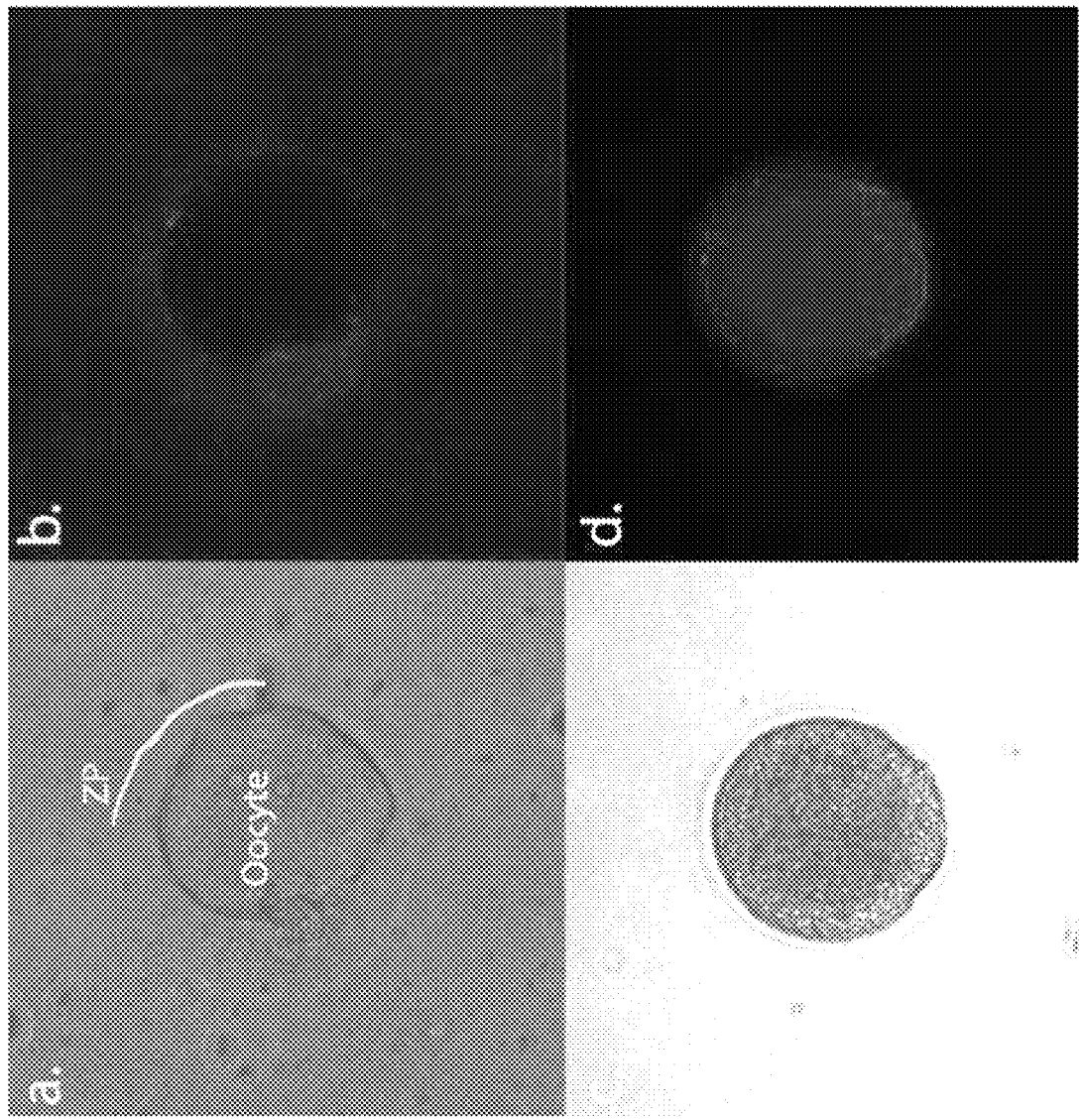

In variations in which the nanostraws are driven against the non-adherent cells, the pressure exerted by the nanostraws may be adjusted or controlled in order to control (e.g., tune) their penetration depth. For example, in FIGS. 7A-7B, applying a moderate pressure during nanostraw delivery results in fluorescently tagged oligomers into the perivitelline space (between ZP and oocyte). By adding further pressure, we can tune the penetration depth to reach into the oocyte itself, as shown in FIGS. 7C-7D. These results present a new avenue to, among other things, generate transgenic animals with high throughput since many embryos can be delivered to simultaneously. Additionally, gene editing tools such as Crispr proteins can be delivered directly through the nanostraws allowing for quick and efficient genetic editing, thereby removing mosaicism commonly associated with creation of transgenic animals.

The tunable access to the perivitelline space could be useful for intracellular sampling applications. For disease screening in embryos, nanostraws may be used to sample (and remove) small amounts of intracellular molecules such as mRNA. In order to have as non-invasive sampling as possible, it would be suitable to sample molecules excreted into the perivitelline space (PVS) rather than from the oocyte itself. The method presented here shows that predictable, tunable access to the PVS or oocyte is possible.

In some variations, a spacer may be used to adjust the depth of the nanostraws advanced into the cells. For nanostraws of diameters 10-1000 nm and lengths of 0.1-25 µm, spacers in the range between 0 and up to 50 times the cell diameter can be used. For spacers larger than 10 times the cell diameter, the nanostraws will not be able to reach the cells for intracellular delivery. A spacer of about half the cell diameter may be suitable for delivery into embryos. When using a spacer of about half the cell diameter, no intracellular delivery was seen, until an additional external force was used to push the nanostraws closer to the cells, as shown in FIGS. 7A-7D. For those spacer thicknesses, adding 150-300 µl mineral oil on top of the cargo solution was useful to tune the nanostraws to reach the intracellular space.

FIGS. 8A-8B illustrate another example of an apparatus that may be used to deliver cargo via nanostraws to non-adherent cells. In general, nanostraws can be incorporated into a microfluidic setup in which biologically relevant cargo can be delivered into non-adherent cells. In such a setup, cells may be transported in microfluidic chambers and interact with nanostraws in one or several of the following ways: pressure, applying an electric and/or magnetic field, controlling osmotic and/or concentration gradients, use of surface interactions and/or species-species interactions, physical inducement such as centrifugal, flow, shear effects, and/or mechanical compression. Such a flow-through device would be able to greatly increase the number of cells that can be delivered into while at the same time being a closed system with minimal risk for contamination. An example of one such embodiment in which a mechanical compression similar to the French press technique is used is shown in FIGS. 8A-8B.

The nanostraw flow-through device in the example shown in FIG. 8A-8B is composed of five layers. Two supportive ITO glass slides 801, 803 (layer 1 and 5) may provide mechanical support as well as electrodes for voltage enhanced delivery. Layers 2 and 4 805, 807 may be laser-cut double sided tape with well-defined thicknesses. Layer 3 809 is a polymer membrane incorporating the nanostraws. FIG. 8B is a top view of an exemplary assembled device with inlets and outlets. Inlets 1 and 3 may be used for microfluidic focusing of the cells. Inlet 2 may be used for the cells. Inlet 4 may be for the cargo solution. Outlet 1 in this example is collecting non-delivered cargo; outlet 2 is for the cells.

A polymer membrane containing the nanostraws (layer 3) 809 is sandwiched between two fluidic chamber layers (layer 2 and 4) 805, 807. The microfluidic path in layer 2 805 may serve two purposes: it may contain the cargo to be delivered, and the fluidic pressure may enable the nanostraws to come in contact with the cells and allow for molecular delivery. Layer 4 807 may serve as a transport channel for the cells. The cell solution and the cargo solution may thus be in fluidic connection through the nanostraw membrane. The three-layer core may be sandwiched between two indium-tin-oxide (ITO) glass slides (Layer 1 and 5) 801, 803 that serve as the supporting structure as well as electrodes for voltage enhanced delivery. Layer 1 incorporates 6 holes for inlet and outlet tubes, as shown in FIG. 8B, which also shows the electrical connections for the electrodes.

During delivery, cells in solution may be injected via inlet 2. In this example, cell culture media is injected via inlet 1 and 3 to microfluidically focus the cells in the delivery area (FIGS. 8A-9B). For intracellular delivery, a cargo solution may be injected via inlet 4. The liquid pressure in the cargo solution may cause the nanostraw membrane to curve, thereby coming in contact with cells that pass through, thereby allowing delivery of molecules into the cells. An electric field can be applied between layers 1 and 5 to enhance the delivery. The cells that were delivered to, can be collected at outlet 2, and the delivery reagent can be recycled at outlet 1. This system can be used for all types of non-adherent cells. FIGS. 10A-10C illustrate the delivery of Dextran blue into HEK293 cells in a similar flow-through apparatus. Staining using calcein AM, revealed very high cell viability. In FIG. 10C the delivery of propidium iodide (PI) into mouse embryos is shown. The PI stains the whole oocyte red, as well as binds to DNA, thereby highlighting the pronuclei. These results show that the nanostraws provide intracellular access also in a flow-through setup.

FIGS. 9A-9B show another example of a flow-through device in use. In FIG. 9A, a side view schematically shows the layout of the exemplary assembled device. Cells are injected through inlet 2, passing by underneath the nanostraws, and are collected at outlet 2. In FIG. 9B, the same side view shows the device during delivery of a cargo into cells flowing through the device. In FIG. 9B, the increased pressure in the cargo reservoir makes the nanostraw membrane bend, thereby coming in contact with the cells, allowing for intracellular access. For enhanced delivery, an electric field, E, can be applied between the two ITO slides (over the nanostraw membrane and the cells, e.g., between the reservoir 905 and the channel 911 that the cells are flowing through). A working area 919 may include a deflectable substrate along a lateral side of the first flow path. The deflectable substrate may include a plurality of nanostraws 917 extending through the deflectable substrate and into the first flow path, wherein the plurality of nanostraws extend from the flexible substrate (e.g., the plurality of nanostraws may be hollow and have an inner diameter of between 5 nm-1500 nm). The apparatus also include a reservoir 913 in fluid communication with an inside of the plurality of nanostraws, the reservoir configured to hold the biologically relevant cargo. In this example, the deflectable substrate is configured to deflect between a first position (shown in FIG. 9A) and a second position (shown in FIG. 9B), further wherein the plurality of nanostraws extend further into the first flow path in the second position than in the first position to at least partially occlude the first flow path and secure non-adherent cell in the flow path against one or more of the plurality of nanostraws.

FIG. 11 illustrates a schematic of a closed-loop apparatus, similar to that shown in FIGS. 9A-9B. A closed loop system may refer to the overall workflow, in which cells 1101 are injected into the device 1103, transformed, and returned in a sterile container 1105. This may reduce user handling, and enable higher numbers of cells to be transfected per unit time. In addition, it may allow the apparatus to be used clinically, where contamination concerns necessitate use of closed-loop devices. For example, the methods and apparatuses described herein may be used with CAR-T cell reprogramming at a local clinic, without need for technicians to manually oversee the transformation process.

FIGS. 12A-12C illustrate another example of a flow-through apparatus similar to that shown in FIGS. 9A-9B. In FIGS. 12A-12C, fluidic pressure may be used to push the nanostraws into the cells. For example, in FIG. 12A, a first fluidic channel 1201 is connected to an input port and an output port (not shown). Non-adherent cells 1203 may be flowed through the channel; the channel may be configured to permit passage of single cells through the channel (e.g., the diameter of the channel may be configured to permit just single cells). A displaceable (e.g., flexible, bendable, movable, etc.) substrate 1205 may be on (and may form) part of the sidewall of the first fluid channel. As described above, the nanostraws may extend through and out of the substrate and into the first fluidic channel. The back of the displaceable substrate may be a reservoir, which may be a second fluidic channel, and may include the cargo (e.g., DNA, RNA, protein, small molecule, etc.). The displacement of the substrate into the microfluidic channel, as shown in FIG. 12B, may apply a gentle pressure by pressing the nanostraws into the cells; releasing the pressure (as shown in FIG. 12C) may allow the cells to flow away.

In the example shown in FIGS. 12A-12C, two overlapping channels, one with the cells flowing through, and the other with the cargo, may be used. Application of fluidic pressure to the cargo channel causes the flexible nanostraw membrane to be pushed up and into the cells, as shown (FIG. 12B). Electric fields, if needed, can be applied through electrodes in the channels to both locally electroporate the cell membrane, and/or to electrophoretically draw cargo into the cell. This second, deflected configuration may be held for some period of time (e.g., between about 0.5-60 seconds, between about 0.5-30 second, between about 1-20 sec, between about 1-15 seconds, etc.) to allow transfer of the cargo into the cells. After this period, the pressure may be released, and flow may be initiated in the cell channel, sweeping the transformed cells to the delivery chamber, and bringing new cells into the delivery region. This can be done on rather large scale, as the DNA and cell culture channels can be designed to be coincident over a large area.

A prototype device of this design is shown in FIG. 13. This device had two cargo ports, a cell input port and cell output port. This prototype was used with GFP plasmid (1 mg/mL cargo) and HEK cells were injected using simple syringe pumps. Pressure was generated whenever the cargo pump was on, and dissipated once it was turned off. Three different cargo channel flow rates were examined to generate 3 different levels of pressure. These resulted in: no delivery; ~30% transfection and a high percentage of cells recovery; and complete crushing of the cells, with no recovery.

As mentioned above, the nanostraws applicable for delivery into non-adherent cells can have diameters ranging from 10 to 1700 nm and lengths ranging from 0.1-50 µm. Their density can be between about $10^4$ to $10^{12}$ nanostraws/cm$^2$. U.S. Pat. No. 9,266,725 describes nanostraw geometry, methods of manufacturing nanostraws, and nanostraw compositions that may be used herein, and are herein incorporated by reference in their entirety. Furthermore, any appropriate cargo solution may be used including a buffer in which the cargo should be diluted can cover a wide range of salt concentrations. The solution in which the cargo is diluted can have an ion concentration ranging from 0 to 10,000 mmol/L. For larger cargo such as plasmid and proteins, the highest delivery efficiency may be found using 0.1×PBS as the buffer to dilute the cargo in, regardless of type and strength of the applied external force, and regardless of cell type. For example, FIGS. 14A-14F show various delivery efficiencies of Cas9 protein into Jurkat cells centrifuged onto 200×1200 nm nanostraws.

In any of the variations described herein an electric field, and particularly a varying electric field, may be used to drive cargo into the cell and/or open the cell to the nanostraw. For example, for nanostraws of diameters 10-1000 nm and lengths of 0.1-50 µm, a pulsed electric field can be applied over the nanostraws in order to aid the delivery of cargo into the cells. Pulse length from 1 µs to 1 s, (e.g., between about 10 µs and 500 µs, between about 50 µs and about 500 µs, between about 150 µs and about 400 µs, about 200 µs, etc.) and pulse frequency from 0.01 Hz to 100,000 Hz (e.g., between about 0.1 Hz and about 50 kHz, between about 1 Hz and about 1 kHz, between about 10 Hz and about 100 Hz, about 10 Hz, about 20 Hz, about 30 Hz, about 40 Hz, etc.), a duration of the applied pulses from about 0.01 sec to 10 h (e.g., about 0.1 sec to about 1 hour, about 1 sec to about 5 minutes, about 10 sec to about 300 sec, between about 40 sec to about 180 sec, etc.). The pulsed field can have any profile, including square/rectangular, sinusoidal, triangular, etc.

Static fields might also work for some applications. The electric field may enhance the transport of charged species through the nanostraws as well as to help permeabilize the cellular membrane just above the nanostraws. The efficiency of the electric field have so far found to be agnostic to the cell types; and exemplary parameters may include a pulse train of 15-25 V, for 150-300 µs, at 30-50 Hz, for 80-120 sec duration. In some variations, higher voltage can give higher transfection efficiency, but may lower the cell viability.

Also described herein are variations in which magnetic particles (e.g., beads) are used, by associating with the non-adherent cell and responding to an externally applied magnetic field to drive the cells associated with the magnetic particles (e.g., beads) into the nanostraws. For example, non-adherent cells may be treated with cyto-protective starch-coated magnetic nanoparticles (MNPs) for magneto-mechanical modulation with nanostraw electroporation (NES). In any of these examples, the MNPs may be added in suspension with the cells and may be taken up by the cells and/or may bind to the outside of the cells. In some variations a crosslinking/binding agent (such as an antibody) may be used to associate cells, including specific cell types from a large pool of different cell types, with magnetic beads so that they may be driven into the nanostraws. As illustrated in FIGS. 16A-16C, the use of magnetic beads in this manner does not reduce the cell viability. For example, FIG. 16A shows that cells exposed to various concentrations of magnetic beads showed similar cell viability and proliferation as control cells. In addition, calcium signals (acute and chronic) were nearly the same across all the different methods. NES with magnet-mechanical modulation generated minimal cellular stresses and unintended perturbations on gene regulations while achieving the highest transfection efficiency and cell viability. Interestingly, actin perturbations using MNPs also promoted membrane resealing after nanostraw electroporation which minimized cell stresses from excessive calcium influx.

FIG. 16A illustrates the cytotoxicity (or lack thereof) of a variety of different starch- and PEG-coated MNPs that had already been incubated with conditioned media for 24 hr. before subsequent incubation with Jurkat cells for another 24 hr. 1 µL/mL and 5 µL/mL of either MNPs were incubated with Jurkat cells with and without stimulation using magnets with field strength of 150 mT, 373 mT and 450 mT previously characterized with a Hall magnetometer. In 1 µL/mL MNP-solution, there were $2.5 \times 10^{12}$ MNPs. Across all the conditions, 1 µL/mL of starch-coated MNPs was the least cytotoxic, as shown in FIG. 16A. Similar results were obtained by monitoring cell proliferation over 4 days following the addition of MNPs with NES, as shown in FIG. 16B. There were no statistical differences in the proliferation between cells in control and conditions with 1 µL/mL of starch-coated MNPs. Other conditions, including only NES, resulted in longer proliferation time, suggesting that starch-coated MNPs are biocompatible and could offer cyto-protective effects. 1 µL/mL of starch-coated MNPs with the 450 mT magnet were used.

In some variations, a 450 mT magnet was placed under NES (30 V, 2 min) during transfection. The magnet provided a maximum magnetic force ($F_{max|mag}$) of 19.0 pN/cell. This mechanism is different from that of magneto-transfection where cargo-bound MNP and cell-seeded magnetic plates are used for longer time, typically overnight. To confirm this, a fluorescent reporter plasmid was added with MNP/magnetic stimulation, but no fluorescent (GFP+) cell was identified. A set-up with a static magnet field below the NES significantly enhanced the net transfection efficiencies from 12.8% to ~30%. Thus, in any of the methods described herein, a static magnetic field may be used. As shown in FIG. 16C, a low frequency alternating magnetic field (to avoid generating heat) did not further enhance transfection efficiencies (e.g., by increasing on/off deformations of the cell membrane through membrane-bound MNPs). FIGS. 16D-16G show that ~30% of Jurkat cells were transfected with the fluorescent-protein reporter plasmid with the nanostraw electroporation-static magnetic field system.

Any of the nanostraw structures described herein may be part of an apparatus (e.g., device, system, etc.), including deices for transfecting or modifying cells. Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A flow-through apparatus for delivering a biologically relevant cargo into non-adherent cells, the apparatus comprising:
   a first flow path having an inlet port and an outlet port, wherein the first flow path is configured to pass a suspension of cells from the inlet port to the outlet port;
   a deflectable substrate along a lateral side of the first flow path;
   a plurality of nanostraws extending through the deflectable substrate and into the first flow path, wherein the plurality of nanostraws extend from the flexible substrate, further wherein the plurality of nanostraws are hollow and have an inner diameter of between 5 nm-1500 nm;
   a reservoir in fluid communication with an inside of the plurality of nanostraws, the reservoir configured to hold the biologically relevant cargo;
   wherein the deflectable substrate is configured to deflect between a first position and a second position, further wherein the plurality of nanostraws extend further into the first flow path in the second position than in the first position to at least partially occlude the first flow path so that non-adherent cell in the flow path communicate with one or more of the plurality of nanostraws.

2. The apparatus of claim 1, further comprising a pair of electrodes on opposite sides of the first flow path configured to apply an electrical field between the reservoir and the first flow path.

3. The apparatus of claim 1, further comprising a pair of electrodes on opposite sides of the first flow path configured to apply an electrical field between the reservoir and the first flow path when the deflectable substrate is in the second position.

4. The apparatus of claim 1, wherein the reservoir is configured as a second fluidic channel through which the biologically relevant cargo flows.

5. The apparatus of claim 1, wherein the first flow path comprises an inlet at a first end and an outlet at a second end.

6. The apparatus of claim 1, wherein the deflectable substrate comprises a porous structure.

7. The apparatus of claim 1, wherein the plurality of nanostraws extend between 2 nm and 50 µm from the substrate.

8. The apparatus of claim 1, wherein the deflectable substrate is configured to transition from the first position to the second position based on the pressure in the reservoir.

9. The apparatus of claim 1, wherein the apparatus is configured as a cartridge.

10. An apparatus for delivering a biologically relevant cargo into non-adherent cells, the apparatus comprising:
　a first flow path having an inlet port and an outlet port, wherein the first flow path is configured to pass a suspension of cells from the inlet port to the outlet port;
　a deflectable substrate along a lateral side of the first flow path;
　a plurality of nanostraws extending through the deflectable substrate and into the first flow path, wherein the plurality of nanostraws extend between 2 nm and 50 µm from the substrate, further wherein the plurality of nanostraws are hollow and have an inner diameter of between 5 nm-1500 nm;
　a reservoir in fluid communication with an inside of the plurality of nanostraws, the reservoir configured to hold the biologically relevant cargo;
　wherein the deflectable substrate is configured to deflect between a first position and a second position, further wherein the plurality of nanostraws extend further into the first flow path in the second position than in the first position to at least partially occlude the first flow path so that non-adherent cell in the flow path communicate with one or more of the plurality of nanostraws; and
　a pair of electrodes on opposite sides of the first flow path configured to apply an electrical field between the reservoir and the first flow path.

* * * * *